United States Patent
Orr et al.

(10) Patent No.: US 7,012,696 B2
(45) Date of Patent: Mar. 14, 2006

(54) OPTICAL HETERODYNE DETECTION IN OPTICAL CAVITY RINGDOWN SPECTROSCOPY

(75) Inventors: Brian J. Orr, East Lindfield (AU); Yabai He, Dundas (AU)

(73) Assignee: Macquarie Research Ltd., NSW (AU)

( * ) Notice: Subject to any disclaimer, the term of this patent is extended or adjusted under 35 U.S.C. 154(b) by 416 days.

(21) Appl. No.: 10/332,924

(22) PCT Filed: Jul. 12, 2001

(86) PCT No.: PCT/AU01/00834

§ 371 (c)(1),
(2), (4) Date: Jun. 9, 2003

(87) PCT Pub. No.: WO02/04903

PCT Pub. Date: Jan. 17, 2002

(65) Prior Publication Data

US 2003/0189711 A1   Oct. 9, 2003

(30) Foreign Application Priority Data

Jul. 12, 2000   (AU) .............................. PO8724
Aug. 30, 2000  (AU) .............................. PO9785

(51) Int. Cl.
*G01B 9/02* (2006.01)

(52) U.S. Cl. .................. 356/454; 356/484; 356/437
(58) Field of Classification Search ............... 356/454, 356/484, 437, 440, 432, 439; 250/343
See application file for complete search history.

(56) References Cited

U.S. PATENT DOCUMENTS

| | | | |
|---|---|---|---|
| 5,528,040 A | 6/1996 | Lehmann | 250/343 |
| 5,815,277 A | 9/1998 | Zare et al. | 356/440 |
| 5,903,358 A | 5/1999 | Zare et al. | 356/437 |
| 5,912,740 A | 6/1999 | Zare et al. | 356/437 |
| 5,984,998 A | 11/1999 | Ottesen et al. | 75/375 |
| 6,015,969 A | 1/2000 | Nathel et al. | 250/227.27 |
| 6,084,682 A | 7/2000 | Zare et al. | 356/437 |
| 6,094,267 A | 7/2000 | Levenson et al. | 356/349 |
| 6,727,492 B1 * | 4/2004 | Ye et al. | 250/227.18 |

FOREIGN PATENT DOCUMENTS

GB     2.197.118 A     5/1988

OTHER PUBLICATIONS

International Search Report in PCT/AU01/00834 dated Sep. 12, 2001.

(Continued)

*Primary Examiner*—Andrew H. Lee
(74) *Attorney, Agent, or Firm*—Marshall, Gerstein & Borun LLP

(57) ABSTRACT

The disclosure relates to optical heterodyne detection cavity ringdown spectroscopy. In one aspect the disclosure relates to an optical system comprising a ringdown cavity cell defining a resonant optical cavity, means for directing coherent light selected from the group consisting of continuous or quasi-continuous light into said optical cavity, means for altering the resonant optical cavity so as to generate a frequency shift of the coherent light in the optical cavity, means for coupling said coherent light into the optical cavity and means for decoupling the frequency shifted coherent light out of said optical cavity, means for optically combining said decoupled frequency shifted coherent light with another portion of coherent light not in optical communication with the optical cavity and means for optical heterodyne detection of the intensity of said combined light. A method for optical detection is also described as well as methods and apparatus for detecting a parameter of a sample.

22 Claims, 12 Drawing Sheets

OTHER PUBLICATIONS

International Preliminary Examination Report in PCT/AU01/00834 dated Feb. 15, 2002.

"Cavity Ringdown Laser Absorption Spectroscopy: History, Development, and Application to Pulsed Molecular Beams", Scherer et al., Chemical Reviews, vol. 97, No. 1, pp. 25–51, 1997.

"Cavity Ringdown Laser Absorption Spectroscopy", Paul et al., Analytical Chemistry, 69, 287 A–292 A, May 1, 1997.

"Observation of CO and $CO_2$ Absorption Near 1.57 $\mu$m with an External–Cavity Diode Laser", Sonnenfroh et al., Applied Optics, vol. 36, No. 15, 3298–3300, May 20, 1997.

"Diode Laser Sensor for Measurements of CO, $CO_2$, and $CH_4$ in Combustion Flows", Mihalcea et al., Applied Optics, vol. 36, No. 33, pp. 8745–8752, Nov. 20, 1997.

The Hitran Molecular Spectroscopic Database and Hawks (Hitran Atmospheric Workstation): 1996 Edition, Rothman et al., J. Quant. Spectrosc. Radiat. Transfer vol. 60, No. 5, pp. 665–710, 1998.

"A Laser–Based Sensor for Measurement of Off–Gas Composition and Temperature in Basic Oxygen Steelmaking", Ottesen et al., Steelmaking Conference Proceedings 1998 (abstract only).

"Optical Heterodyne Detection in Cavity Ring–Down Spectroscopy", Levenson et al., Chemical Physics Letters 290, pp. 335–340, Jul. 3, 1998.

"A Laser–Based Sensor for Measurement of Off–Gas Composition and Temperature in Basic Oxygen Steelmaking", Ottesen et al., Scandinavian Journal of Metallurgy, 1999 (abstract only).

"Cavity–Ringdown Spectroscopy, An Ultratrace–Absorption Measurement Technique", ACS Symposium Series 720, American Chemical Society, Washington, D.C., 1999 (index pages only).

"Optical Method and Tunable Laser–Beam Apparatus for Monitoring the Off–Gas Composition in Steelmaking", Ottesen et al., Int. Appl. WO 99/26058 A1, May 27, 1999 (abstract only).

"Cavity Ring–Down Spectroscopy: Experimental Schemes and Applications", Berden et al., Int. Reviews in Physical Chemistry, vol. 19, No. 4, pp. 565–607, 2000.

"Ringdown and Cavity–Enhanced Absorption Spectroscopy Using a Continuous–Wave Tunable Diode Laser and a Rapidly Swept Optical Cavity", He et al., Chemical Physics Letters 319, pp. 131–137, Mar. 10, 2000.

"Multiplexed Continuous–Wave Diode–Laser Cavity Ringdown Measurements of Multiple Species", Totschnig et al., Applied Optics, vol. 39, No. 12, pp. 2009–2016, Apr. 20, 2000.

"In Situ Combustion Measurements of CO with Diode–Laser Absorption Near 2.3 $\mu$m", Wang et al., Applied Optics, vol. 39, No. 30, pp. 5579–5589, Oct. 20, 2000.

"Rapidly Swept, Continuous–Wave Cavity Ringdown Spectroscopy with Optical Heterodyne Detection: Single– and Multi–Wavelength Sensing of Gases", Applied Phys. B 75, pp. 267–280, 2002.

"Stable Isotope Ratios Using Cavity Ring–Down Spectroscopy: Determination of $^{13}C/^{12}C$ for Carbon Dioxide in Human Breath", Crosson et al., Analytical Chemistry, vol. 74, No. 9, pp. 2003–2007, May 1, 2002.

* cited by examiner

OPTICAL HETERODYNE DETECTION IN OPTICAL CAVITY RINGDOWN SPECTROSCOPY

This is the U.S. national phase of International Application No. PCT/AU01/00834 filed Jul. 12, 2001, the entire disclosure of which is incorporated herein by reference.

TECHNICAL FIELD

The present invention relates to optical absorption spectroscopy and in particular is directed to a method and apparatus for optical heterodyne detection using an optical ringdown cavity cell.

BACKGROUND OF THE INVENTION

The detection of trace and weakly absorbing gas-phase species is of importance in scientific, industrial, medical, agricultural and environmental spectroscopic sensing applications. In recent years optical cavity ringdown laser absorption spectroscopy (CRDS) has become a new analytical technique for determination of such trace concentrations. The technique is simple, quick, versatile and an accurate way to acquire weak optical absorption spectra, the method typically able to make optical absorption measurements with sensitivities of the order of $10^{-7}$ per cm of sample. General information on CRDS is obtainable for example from U.S. Pat. No. 5,528,040 by Lehmann, "Cavity Ringdown Laser Absorption Spectroscopy: History, Development and Application to Pulsed Molecular Beams" in *Chemical Reviews* 97 (1997) 25–51 by J. J. Scherer, J. B. Paul, A. O'Keefe, R. J. Saykally, and "Cavity-Ringdown Spectroscopy—An Ultratrace-absorption Measurement Technique", edited by K. W. Busch and M. A. Busch, ACS Symposium Series (1999) No. 720, ISBN 0-8412-3600-3.

CRDS involves injecting monochromatic light into an optical cavity acting as a high-finesse stable optical resonator (Fabry-Perot optical cavity) formed by two highly reflecting input and output mirrors. A portion of the light incident on one of the mirrors enters the optical cavity and is multiply reflected. When no sample is present in the optical cavity, radiant energy injected into the resonator decreases in time following an exponential decay with a ringdown time $\tau$ which is dependent on the reflectivity of the mirrors, their separation and the speed of light in the optical cavity. When a sample is present in the optical cavity, the radiant energy decrease is accelerated at those wavelengths where optical absorption with the sample occurs resulting in a shorter ringdown time $\tau$. An optical absorption spectrum for the sample gas is obtained by placing a detector after the output mirror to detect light emerging from the optical cavity and plotting the energy loss rate which is the reciprocal of the ringdown time (the time profile of light emerging from the optical cavity) versus the wavelength (frequency) of the incident light and comparing this with the optical absorption spectrum of the empty optical cavity. The shape or profile of the resulting plot changes with absorbing species present. For sufficiently weak optical absorption, the ringdown rate increases linearly as optical absorbance or optical absorption coefficient of the sample medium.

CRDS has the advantage that because it is measuring time decay and not amplitude of light it is insensitive to fluctuations in amplitude of light (optical intensity) generated by the light source and is thereby highly sensitive.

As indicated above CRDS is generally capable of detecting optical absorption to a sensitivity of the order of $10^{-7}$ per cm of a sample. In certain circumstances, particularly for detecting low concentrations of absorbing species in gases, it would be desirable to achieve greater sensitivities. Detection at greater sensitivities however is not readily attainable with current CRDS systems where problems such as optical feedback, noise present in detection electronics and large optical losses in the systems are present. Further many of the prior art apparatus require the use of large pulsed lasers which are not amenable to portability and are therefore unsuitable in many applications.

OBJECT OF THE INVENTION

It is the object of the present invention to overcome or substantially ameliorate at least one of the above disadvantages or at least provide a suitable alternative.

SUMMARY OF THE INVENTION

According to a broad aspect of this invention there is provided an optical system comprising:

a ringdown cavity cell, said cell defining a resonant optical cavity;

means for directing coherent light selected from the group consisting of continuous or quasi-continuous light into said optical cavity, means for altering the resonant optical cavity so as to generate a frequency shift of said coherent light in said optical cavity, means for coupling said coherent light into said optical cavity, means for decoupling the frequency shifted coherent light out of said optical cavity, means for optically combining said decoupled frequency shifted coherent light with another portion of coherent light not in optical communication with said optical cavity, and means for optical heterodyne detection of the intensity of said combined light.

The system may further comprise:

a coherent light source suitably a continuous-wave laser disposed to enable said means for directing to direct a portion of coherent light from said source into said optical cavity.

According to another aspect of the invention, there is provided an optical apparatus including a ringdown cavity cell, said cell defining a resonant optical cavity in optical communication with a portion of coherent light selected from the group consisting of continuous and quasi-continuous light emitted from a coherent light source, means for directing said portion of coherent light into said optical cavity, means for altering the resonant optical cavity so as to generate a frequency shift of coherent light in the optical cavity, means for coupling said coherent light into said optical cavity and decoupling the frequency shifted coherent light from the optical cavity, means for optically combining said frequency shifted light with another portion of coherent light not in optical communication with said optical cavity and means for optical heterodyne detection of the intensity of said combined light.

Suitably the apparatus further comprises a sample contained in the ringdown cavity cell and means for determining a parameter of the sample.

Suitably one or more optical fibres are provided for directing the light into the optical cavity and/or into a polariser and/or for combining the decoupled and uncoupled light.

According to a further aspect, there is provided a method for optical detection including emitting coherent light selected from the group consisting of continuous and quasi-continuous light from a coherent light source, directing a portion of said coherent light from said coherent light source to a resonant optical cavity of a ringdown cavity cell, the cell defining a resonant optical cavity in optical communication with the coherent light source, altering the resonant optical cavity so as to generate a frequency shift of coherent light in the optical cavity, coupling said coherent radiation into said optical cavity and decoupling the frequency shifted coherent light out of the optical cavity, optically combining the decoupled frequency shifted coherent light with a portion of coherent light from said coherent light source not in optical communication with said optical cavity and optical heterodyne detecting the intensity of said combined light.

Suitably the method further comprises determining a parameter of a sample contained in the ringdown cavity cell.

According to an additional aspect, there is provided an optical apparatus including:
 a continuous-wave laser source for emitting radiation;
 a ringdown cavity cell, said cell defining a resonant optical cavity in optical communication with said laser;
 means for directing a portion of said radiation emitted from said light source into said optical cavity of said ringdown cavity cell;
 means for coupling and decoupling said radiation into said optical cavity without using an optical switch or modulator;
 means for generating a frequency shift of the radiation in the optical cavity without using an optical modulator;
 means for optically combining a portion of said radiation emitted from said laser source and which has not been emitted from said optical cavity with frequency shifted ringdown cavity radiation which is emitted from the optical cavity, wherein the combined radiation is capable of optical heterodyne detection; and
 means for optical heterodyne detection of said combined radiation.

According to another aspect of the invention, there is provided an optical apparatus for determining a parameter of a sample including:
 a continuous-wave laser source for emitting radiation;
 a ringdown cavity cell containing said sample, said cell defining a resonant optical cavity in optical communication with said light source;
 means for directing a portion of said radiation emitted from said light source into said optical cavity of said ringdown cavity cell;
 means for coupling and decoupling said radiation into said optical cavity without using an optical switch or modulator;
 means for generating a frequency shift of the radiation in the optical cavity without using an optical modulator;
 means for optically combining a portion of said radiation emitted from said laser source and which has not been emitted from said optical cavity with frequency shifted ringdown cavity radiation which is emitted from the optical cavity, wherein the combined radiation is capable of optical heterodyne detection;
 means for optical heterodyne detection of said combined radiation; and
 means for determining a parameter of the sample.

According to a further aspect of the invention, there is provided a method for optical detection including:
 emitting radiation from a continuous-wave laser source;
 directing a portion of said radiation emitted from said laser into a resonant optical cavity of a ringdown cavity cell, said resonant optical cavity in optical communication with said laser;
 coupling and decoupling said radiation into said optical cavity without using an optical switch or modulator;
 generating a frequency shift of the radiation in the optical cavity without using an optical modulator;
 optically combining a portion of said radiation emitted from said laser source and which has not been emitted from said optical cavity with frequency shifted ringdown cavity radiation which is emitted from the optical cavity, wherein the combined radiation is capable of optical heterodyne detection; and
 optically heterodyne detecting said combined radiation.

According to another aspect of the invention, there is provided an optical method for determining a parameter in a sample including:
 emitting radiation from a continuous-wave laser source;
 directing a portion of said radiation emitted from said laser source into a resonant optical cavity of a ringdown cavity cell containing said sample, said resonant optical cavity in optical communication with said light source;
 coupling and decoupling said radiation into said optical cavity without using an optical switch or modulator;
 generating a frequency shift of the radiation in the optical cavity without using an optical modulator;
 optically combining a portion of said radiation emitted from said laser source and which has not been emitted from said optical cavity with frequency shifted ringdown cavity radiation which is resonant with said optical cavity and which is emitted from the optical cavity, wherein the combined radiation is capable of optical heterodyne detection;
 optically heterodyne detecting said combined radiation; and
 determining a parameter of the sample.

According to a further aspect, there is provided an optical apparatus including:
 at least two continuous-wave laser sources for emitting laser radiation, each source operating at a different wavelength;
 a ringdown cavity cell, said cell defining a resonant optical cavity in optical communication with said at least two lasers;
 means for directing a portion of said laser radiation emitted from said at least two lasers into said optical cavity of said ringdown cavity cell;
 means for coupling and decoupling said laser radiation into said optical cavity;
 means for generating a frequency shift of the laser radiation in the optical cavity without using an optical modulator;
 means for optically combining a portion of said laser radiation emitted from said laser source and which has not been emitted from said optical cavity with frequency shifted ringdown cavity laser radiation which is emitted from the optical cavity, wherein the combined radiation is capable of optical heterodyne detection; and
 means for optical heterodyne detection of said combined radiation.

Suitably the apparatus further comprises a sample contained in said optical cavity and means for determining a parameter of the sample.

Suitably the apparatus includes one or more optical fibres for directing said portion of laser radiation into said cavity and/or into a polariser and/or for combining said decoupled and uncoupled radiation.

According to an additional aspect of the invention, there is provided a method for optical detection including:
 emitting laser radiation from at least two continuous-wave laser sources, each laser operating at a different wavelength;
 directing a portion of said laser radiation emitted from said lasers into a resonant optical cavity of a ringdown cavity cell, said resonant optical cavity in optical communication with said at least two lasers;

coupling and decoupling said laser radiation into said optical cavity;

generating a frequency shift of the laser radiation in the optical cavity without using an optical modulator;

optically combining a portion of said laser radiation emitted from said laser source and which has not been emitted from said optical cavity with frequency shifted ringdown cavity laser radiation which is emitted from the optical cavity, wherein the combined radiation is capable of optical heterodyne detection; and optically heterodyne detecting said combined radiation.

Suitably the method also includes determining a parameter of a sample contained in the ringdown cavity cell.

According to another aspect, the present invention consists in an optical apparatus including:

at least one continuous-wave laser source for emitting laser radiation at a specified wavelength;

at least two ringdown cavity cells, each cell defining a resonant optical cavity in optical communication with at least one of said continuous-wave lasers;

means for directing a portion of said laser radiation emitted from said laser into an optical cavity of at least one of the ringdown cavity cells;

means for coupling and decoupling said laser radiation to said optical cavity;

means for generating a frequency shift of the laser radiation in the optical cavity without using an optical modulator;

means for optically combining a portion of said laser radiation emitted from said laser source and which has not been emitted from said optical cavity with frequency shifted ringdown cavity laser radiation which is emitted from the optical cavity, wherein the combined radiation is capable of optical heterodyne detection; and means for optical heterodyne detection of said combined radiation.

Suitably the apparatus further comprises a sample contained in said optical cavity and means for determining a parameter of the sample.

Suitably the apparatus includes one or more optical fibres for directing said portion of laser radiation into the cavity and/or polariser and/or for combining said decoupled and uncoupled radiation.

According to a further aspect, there is provided a method for optical detection including:

emitting laser radiation from at least one continuous-wave laser source having a specified wavelength;

directing a portion of said laser radiation emitted from said lasers into a resonant optical cavity of at least one of the ringdown cavity cells, said resonant optical cavity in optical communication with said laser;

coupling and decoupling said laser radiation into at least one of said cavities;

generating a frequency shift of the laser radiation in said optical cavity without using an optical modulator;

optically combining a portion of said laser radiation emitted from said laser source and which has not been emitted from said optical cavity with frequency shifted ringdown cavity laser radiation which is emitted from the optical cavity, wherein the combined radiation is capable of optical heterodyne detection; and optically heterodyne detecting said combined radiation.

DESCRIPTION OF PREFERRED EMBODIMENTS OF THE INVENTION

The coherent light source is selected from a continuous coherent light source (i.e., with constant amplitude in time) and a quasi-continuous coherent light source. Suitable coherent light sources include many form of laser but are not confined to lasers. For instance, a suitable coherent continuous or quasi-continuous light source can be based on non-linear optics, in various forms such as: an optical parametric oscillator (OPO); a laser-pumped wavelength converter involving second-harmonic generation (SHG), third-harmonic generation (THG), sum-frequency generation (SFG), difference-frequency generation (DFG), or stimulated Raman scattering (SRS).

One suitable form of quasi-continuous coherent light source is suitably generated by a long-pulse laser or coherent optical source. Its optical power needs to be established at a constant plateau level well in advance of the point in the cavity sweep cycle at which the optical cavity comes into resonance with the light while optical power builds up in the cavity. To observe readily interpreted CRDS signals, the duration of the plateau value of incident optical power needs to be substantially longer (e.g., by a factor of 10) than the sum of build-up time and ringdown decay time, so that the incident optical power is effectively constant during the build up and decay cycle.

Another suitable form of quasi-continuous coherent light source generates a train of short optical pulses that occur at a constant repetition rate and with a period that is short relative to the build-up time of light in the optical cavity. Such a pulse train is suitably generated by a mode-locked laser or coherent optical source. The peak amplitude of the pulse train needs to be established at a constant plateau level of coherent optical power well in advance of the point in the cavity sweep cycle at which the optical cavity comes into resonance with the light while optical power builds up in the cavity. To observe readily interpreted CRDS signals, the period between pulses in the train needs to be substantially shorter (e.g., by a factor of 10) than the build-up time for the optical cavity resonance. Moreover, the duration of the plateau value of incident optical peak power needs to be substantially longer (e.g., by a factor of 10) than the sum of build-up time and ringdown decay time, so that a steady state of incident radiation prevails throughout the build up and decay cycle.

Suitably the coherent light source used is a continuous-wave (cw) laser, suitably a semiconductor diode laser. Suitably one coherent light source is used, although in some embodiments more than one coherent light source can be used (e.g. two, three or more lasers), each coherent light source suitably having a different wavelength. By use of multiple coherent light sources it is possible to detect the presence of more than one parameter of said sample or alternatively confirm the presence of a parameter. Diode lasers are typically small and inexpensive enabling an apparatus to be designed for portability and compactness. Continuous-wave (cw) lasers are superior to pulsed lasers due to the narrower optical bandwidth of the continuous-wave (ew) laser output and the narrowband filtering role of the ringdown optical cavity. The laser suitably generates light comprising a wavelength corresponding to an optical absorption region of interest in a sample, preferably a gaseous sample. Preferably the continuous-wave (cw) laser used emits infrared, ultraviolet, or visible wavelengths, typically infrared. Accordingly the term radiation as used is the present specification is intended to include light at these wavelengths. Suitably the laser is selected from infrared lasers, diode lasers, and single mode tunable continuous-wave (cw) dye lasers which may include a temperature controller. Suitable lasers also include distributed feedback lasers, external optical cavity lasers and optical fibre lasers.

The laser can be monochromatic or wide-spectrum provided means are provided to control its wavelength, which control may be part of the laser itself or a component situated in the apparatus. Suitably the laser has an optical bandwidth of less than 10 MHz.

The ringdown cavity cell is suitably a linear or folded optical cavity or a ring resonator such as described in U.S. Pat. No. 5,912,790. Preferably the ringdown cavity cell is a linear cell of two reflectors suitably two highly reflective dielectric input and output mirrors having a concave curvature designed to retain light in the optical cavity. Suitable radii of curvature of the mirrors are in a range of 0.1 to 10 meters, typically about 1 meter. A stable, low-loss optical cavity is formed from the two mirrors being aligned with respect to the optical axis of the cell, the mirror separation typically being less than twice the radius of curvature. Suitably the effective intracavity optical pathlength for optical absorption is two to five orders of magnitude greater than the physical length of the optical cavity. Suitable distances between the optical cavity mirrors are less than 1 meter, more preferably of the order of 50 to 500 mm. The distance is suitably adjusted to optimise separation of low-order transverse optical cavity modes. Suitable mirrors for use in the invention are well known in the art and are suitable for use over a wide range of the visible, ultraviolet and infrared spectrum. Suitable mirrors used typically have reflectivity greater than 99.95% and up to 99.999% enabling most radiation entering the optical cavity to be reflected over pathlengths of the order of about $10^4$ times the physical length of the cell thereby providing a long effective optical absorption path length within the optical cavity and providing ringdown time of a few microseconds. Suitably a sample is provided in the cell, preferably a sample gas which can be provided in the cell by flowing gas through a narrow tube coaxial with the optical axis of the ringdown cavity cell. Suitable gases which can be detected by use of the method and apparatus of the invention include $CO_2$, $CO$, $H_2O$ vapour, $NO$, $NH_3$, $HF$, $HCN$, nerve gas, phosgene, oxygen, nitrous oxide, methane, light alkanes, ethylene, acetylene, ethanol, acetaldehyde, ketones and chloroform. Combinations of gases can also be detected and if necessary in order to do so, more than one coherent light source suitably continuous-wave sources can be used having wavelengths corresponding to wavelengths of the optical absorption regions of the gases of interest. The ringdown cavity cell can be formulated as a separate module from the remaining apparatus so that it can be used in remote sensing applications. Certain properties of solid and liquid samples can also be measured using CRD spectroscopy by depositing small amounts of a sample to the coating surface of at least one ringdown cavity mirror/reflector. Alternatively an extra environmental sensitive mirror can be contained in the cavity so as to form a triangular cavity able to detect environmentally sensitive parameters.

The means for directing a portion of said coherent light/radiation emitted from the coherent light source/continuous wave laser to the ringdown cavity cell ensures that the light/radiation emitted from the light source/laser follows an optical path into the ringdown cavity cell. Suitably the means for directing a portion of said light/radiation is provided by one or more beam splitters, a polarising beam splitter, one or more optical isolators, a reflector, focusing lens, polarising prism, waveplate, Faraday rotator, optical fibre or optical circulator. In one embodiment a portion of the light/radiation is directed into the cell by means of a beam splitter. Suitably such a beam splitter directs at least 50%, more preferably at least 90%, most preferably at least 99% of the emitted light/radiation to the input of the ringdown cavity cell. In some embodiments, the preferred form of beam splitter is a polarising beam splitter. Suitably the light/radiation emitted from the light source/laser is first passed through an isolator such as a Faraday isolator which provides a one-way transmission path allowing light/radiation to travel away from the light source/laser but preventing light/radiation from travelling in the opposite direction. The isolator thereby protects the light source/laser from back reflections or optical feedback which tend to increase laser noise. Suitably the isolator has a 30 to 60 dB rating. The light/radiation is preferably coupled into the optical cavity by means of a combination of any one of at least one reflector, a polarisation control optics means and a focusing lens system (suitably a 5 cm to 5 m lens, either single or compound, more typically a 40 cm focal-length lens) which collects and focuses the light/radiation into the optical cavity. The polarisation control optics means functions to direct backward propagating light to the detection means (suitably a photodetector) and control the polarisation of light incident on the detecting means and/or on the input of the optical cavity cell. Suitably the polarisation control optics means comprises a polarising prism/beam splitter, waveplate, optical circulator or Faraday rotator. Typically, the polarisation control optic means comprises a polarising beam splitter and a Faraday rotator, or a polarising beam splitter and a quarter-wave plate or an optical circulator. The rotation angle of a Faraday rotator and thickness of a quarter-wave plate are wavelength dependent. Accordingly some polarising beam splitters can be designed for working in a narrow wavelength region and specified by their designed centre wavelengths. Accordingly it is desirable to select the polarising beam splitters on the basis of the wavelengths of interest as operating at wavelengths far away from the designed wavelengths will result in a reduction of coupling efficiency of the backward-propagated light to the detecting means. Different optical material can be used to fabricate the polarisation control optics for different wavelength regions. In embodiments where more than one ringdown cavity cell is used and/or more than one coherent light source is used, it may be desirable to include in the optical path a combiner/multiplexer, an optical switch, switch module or optical fibre splitter so as to distribute the laser and return ringdown light to and from the different locations at which the ringdown cavities are positioned or to switch between the various wavelengths of the lasers.

In accordance with the present invention there is provided a means for coupling and decoupling the light/radiation to and from the optical cavity. Such means is typically provided by a piezoelectric translator (PZT) operated to provide movement (preferably continuous) of at least one of the reflectors/mirrors contained in the optical cavity cell so as to vary the length of the optical cavity. The duration of the movement is suitably rapid with respect to the ringdown time. The light/radiation can be most efficiently coupled into the optical cavity under optical resonance conditions, where the round-trip optical cavity length is an integer multiple of the wavelength of the light/radiation. Suitably the reflector/mirror is moved rapidly by mounting the reflector/mirror on a cylindrical piezoelectric translator (PZT) with its sweep controlled by a triangular or saw-tooth or other complex form of ramp voltage operated by an electronic control circuit. Suitable optical cavity length shifts are of the order of 1 nm to 1 $\mu$m and are typically applied on a time scale that is shorter than the ringdown time of the optical cavity so as to shift the ringdown cavity on and off resonance, as ringdown cavities have high finesse (typically>$10^4$). The PZT sweep amplitude typically approximates one wavelength of the light in the optical cavity, thereby ensuring that one strong optical cavity resonance occurs in each PZT sweep half-cycle. Optical energy is built up and stored in the optical cavity as any of its modes moves into resonance with the wavelength of the light, and the optical cavity then transmits more light. The decay of light energy that is built up and stored in the optical cavity during the short resonance interval is observable after the optical cavity has moved off resonance, because the input light is effectively blocked by the highly reflective optical cavity reflectors/mirrors during the (relatively long) off resonance interval. The decay of light energy is gradual with a ringdown time constant τ that depends on the reflector/mirror reflectivity and the optical absorption of the optical medium in the optical cavity.

It should be noted that, with the use of continuous-wave (cw) lasers, the source of light is constant and accordingly there is not necessarily any observable ringdown signal. By use of the present invention and in particular in preferred embodiments by moving the reflector/mirror rapidly with respect to the ringdown time it is possible to retain the continuous-wave while generating a suitable ringdown signal. It is then possible to avoid the need to cut off or modulate the intensity of the light by use of expensive fast optical switches such as electro-optic modulators, Pockels cells, electro-optic Kerr cells or acousto-optic modulators and without the need to lock the optical cavity length and laser wavelength to each other. Further by exclusion of such devices, it is possible to make the apparatus more compact.

A means for shifting the optical frequency of the light/radiation in the optical cavity is intrinsic to the invention. Such means is typically provided by a piezoelectric translator PZT) operated to provide movement (preferably continuous) of at least one of the reflectors/mirrors contained in the cell so as to alter the length of the cavity. A Doppler-type frequency shift occurs each time the light/radiation inside the optical cavity is reflected from the moving mirror. The frequency of the light/radiation inside the optical cavity follows the change of the optical cavity resonance frequency as the optical cavity mirror moves and is different from the originally emitted light frequency. Depending on the distance of mirror movement, the amount of frequency shift is typically in the range of MHz to GHz (for a typical amplitude of mirror travel, the resulting frequency shift spans the range 0–100 MHz, typically 0 to 10 MHz). The Doppler-type frequency shifts $\Delta v_j$ that occur with each reflection of intracavity radiation from a continuously moving mirror can be represented by the following equation:

$$\Delta v_j = (v_{j+1} - v_j) = v_j(2v/c) \tag{1}$$

where $v_j$ is the frequency of light on its jth round trip in the optical cavity, v is the mirror velocity and c is the speed of light. The frequency of light/radiation inside the optical cavity differs by $\Delta v$ (summed over multiple passes in the optical cavity) from that of the incident light/radiation; it follows the change of the optical cavity resonance frequency as the optical cavity reflector/mirror is swept. A distribution of intracavity optical fields is therefore generated during multiple passes of the rapidly swept optical cavity. The frequency distribution of these intracavity field components is relatively narrow at any instant, because the amplitude of each decays such that its frequency follows the change of optical cavity resonance frequency as the position of the optical cavity reflector/mirror is varied. Modulated optical cavity ringdown signals then arise as the accumulated Doppler-shifted optical fields in the optical cavity interfere with each other and with the (unshifted) incident light/radiation.

An alternative interpretation of the apparatus is to regard the entire optical cavity with its rapidly swept mirror/reflector as a single active optical element. As the reflector is swept, the length of the optical cavity and its resonant wavelengths vary. For a particular incident wavelength, the dynamics of this rapidly swept cavity then determines the amplitude of transmitted and reflected light that builds up and decays on the time scale of the optical cavity sweep.

It is within the scope of the present invention to use a single Doppler shift. Suitably an abrupt mirror displacement of a well-defined amplitude that shifts the effective optical heterodyne detected frequency further above that of low-frequency technical noise.

It will be apparent that the means for shifting the frequency of the radiation in the optical cavity and the means for coupling and decoupling the radiation to said optical cavity may be the same. It will also be appreciated that the means for directing and the means for combining the light/radiation may also be the same.

Suitably the light/radiation emitted from the coherent light source suitably a continuous-wave (cw) laser which has not been emitted from the optical cavity and which is combined with the frequency shifted ringdown light/radiation is light/radiation which either (a) has not passed through the cell but has been back-reflected off the cell and/or (b) light/radiation that has purposely been redirected by use, for example of at least one beam splitter. The frequency shifted ringdown light/radiation which is combined is either ringdown light/radiation emerging from the input mirror/reflector and/or ringdown radiation emerging from the output mirror/reflector. By ensuring the combination of emitted light/radiation with frequency shifted ringdown light/radiation it is possible to obtain an intense detectable wave which is the product of two fields containing a strong radiation component corresponding to the emitted laser light/radiation coupled with a weak ringdown light/radiation component which varies in accordance with the frequency shift. The method of the invention thereby enables optical signals related to the ringdown time to be detected at a high modulation frequency rather than at the low frequency of the original ringdown signal enabling more sensitive detection.

The preferred mode of detection used is described in common parlance as optical heterodyne detection. The Macquarie Dictionary, $2^{nd}$ Edition, The Macquarie Library Pty Ltd defines heterodyne as denoting or pertaining to a method of receiving continuous-wave radiotelegraph signals by impressing upon the continuous radiofrequency oscillations another set of radiofrequency oscillations of a slightly different frequency, the interference resulting in fluctuations or beats of audiofrequency. The Macquarie Dictionary, $2^{nd}$ Edition, The Macquarie Library Pty Ltd defines homodyne as a radio receiver which demodulates an amplitude-modulated signal by the process of mixing the carrier signal with the sidebands. Expert opinion is divided as to whether the detection mode used is true heterodyne (ie., detected at the difference frequency between signal and local oscillator waves) or whether it is actually homodyne (ie., detected in the frequency domain shared by the signal and local oscillator waves). The descriptions 'heterodyne' and 'homodyne' are therefore used interchangeably in this context.

The means for optical heterodyne detection of the combined light/radiation is suitably provided by means of at least one photodetector, typically a square-law photodetector. In some embodiments at least two photodetectors may be required. The photodetector(s) are suitably coupled to a preamplifier (suitably up to a 500 MHz maximum bandwidth, more preferably 10 to 100 MHz) and optionally a data acquisition device such as an A/D converter, a digital oscilloscope or a boxcar integrator system. The detector detects the combined light/radiation measuring the interaction of a sample contained within the optical cavity with intracavity light/radiation. The combined light/radiation is converted by the photodetector into a corresponding signal. Suitable photodetectors include photomultiplier tubes, semiconductor pin photodiodes and avalanche photodiodes. Ge, AlGaAs, InGaAs and HgCdTe photodiodes are suitable. The photodetector can be located before and/or after the ringdown cavity cell. In one embodiment, the photodetector is located before the ringdown cavity cell and is preferably located along an optical light path different to that of the incoming light/radiation. This can be achieved by use of a polarising beam splitter and a polarisation controller. In another embodiment the photodetector is located after the ringdown cavity cell, prior to reaching the photodetector, a portion of the emitted light/radiation is suitably directed by means of a beam splitter and a number of reflectors prior to combination with ringdown light/radiation emerging from the output of the ringdown cavity cell, suitably by means of a beam splitter. In another embodiment two photodetectors are used, one located before the ringdown cavity cell and one after the ringdown cavity cell. In such an embodiment the photodetector located before the ringdown cavity cell suitably detects the combined light/radiation as above, and the second photodetector detects ringdown light/radiation emerging from the output of the ringdown cavity cell.

Means for determining a parameter of a sample is suitably a data analysis and recording device such as a computer. Various parameters of interest which can be determined from the photodetector signals include ringdown rates and the time dependence of the light intensity. The decay rate of the combined light/radiation is suitably determined by amplifying, rectifying and digitising and fitting the waveform to an envelope with a first-order exponential decay, using a suitable algorithm. The decay curve is indicative of the optical absorption of a sample. By comparison with an empty cell decay rate it is possible to determine the level of trace species in a sample or the optical absorption spectra of a known composition. The decay curve can also be correlated to other parameters aside from absorption, including light scattering, reflectivity and dielectric relaxation or any other parameter that causes an energy change as a result of the interaction between the frequency shifted light/radiation and the sample. By use of more than one coherent light source (each source having a different wavelength) it is also possible to determine the presence of more than one trace species in a sample (each trace species having different optical absorption wavelengths) or alternatively confirm the presence of a trace species having multiple optical absorption wavelengths In a typical embodiment of the invention, a triangular (or ring) ringdown cavity is assembled by introducing a third mirror, the reflectivity of which is designed to be sensitive to its environment, such as temperature, pressure, humidity, external electric or magnetic fields or pressure/concentration of a particular chemical species (e.g., one that adsorbs on the surface of the third mirror). It is possible to couple the intracavity optical field via an evanescent wave to a medium or environmental conditions that are external to the cavity itself This approach is similar to certain forms of fibre-optic sensor, but CRDS offers the prospect of much higher sensitivity. Suitably in this embodiment the angle between the incident and reflected beams on the mirror/reflector connected to the PZT is as small as possible.

In another typical embodiment of the invention, optical fibres are used to transmit the light/radiation over various portions of the beam path, for example, between the laser and the ringdown cavity cell. Hence in one embodiment, the means for directing a portion of said light/radiation comprises an optical fibre and/or the means for combining a portion of said light/radiation emitted with frequency shifted light/radiation comprises an optical fibre. By use of optical fibres it is possible to remotely isolate the optical cavity cell from the light source and detection system, thereby facilitating environmental, agricultural, clinical and industrial monitoring applications. In such embodiments it is possible to control the PZT by a separate voltage source, by electrical connection to the control means or by wireless means. Suitable optical fibres include silica fibres (which cut out at about 1.8 $\mu$m) and fluoride glass fibres (which can operate up to 3 $\mu$m).

By use of the apparatus and method of the invention it is possible to make efficient use of all available laser output energy and thereby enhance the detection sensitivity of optical cavity ringdown spectroscopy by several orders of magnitude. Such sensitivity may be of the order of $10^{-11}$ per cm of sample. Typically very weak optical absorption per unit length ($cm^{-1}$) with high noise limited sensitivities of $3\times10^{-9}$ $cm^{-1}$ to $4\times10^{-9}$ $cm^{-1}$ or even higher can be achieved. Dynamic ranges of at least 35 dB are also capable by use of the apparatus and method of the invention. The dynamic range is that range over which linear signal detection is possible and depends on other factors such as the noise level.

By means of the present invention it is possible to use a rapidly swept or stepped optical cavity in a novel approach to optical cavity ringdown spectroscopy (CRDS) suitably with a continuous-wave (cw) laser. The frequency of the optical light/radiation trapped inside the optical cavity is suitably shifted by moving at least one optical cavity mirror/reflector. The frequency-shifted optical cavity ringdown light/radiation is then suitably combined efficiently with the original light/radiation enabling generation of an optical heterodyne signal. (An alternative view of this process treats the entire optical cavity with its moving mirror/reflector as a single active optical element with resonant properties depending on the mirror/reflector movement.) Measurement of cw-CRDS signals by this optical heterodyne approach enhances the detection sensitivity by several orders of magnitude. The resonance properties of a swept optical cavity also simplify cw-CRDS in that they eliminate the need for a fast optical switch and avoid locking of the optical cavity length and laser wavelength to each other although optical switches may still be desirable in some applications. By use of the apparatus and methods of the invention it is possible to obtain ultra-sensitive, high-resolution, accurate CRD spectroscopy with relatively simple, inexpensive, compact apparatus suitable for use in the field or at industrial sites or in clinical situations.

BRIEF DESCRIPTION OF THE DRAWINGS

A preferred form of the present invention will now be described by way of example with reference to the accompanying drawings wherein.

DETAILED DESCRIPTION OF THE PREFERRED EMBODIMENTS

Figure 1:
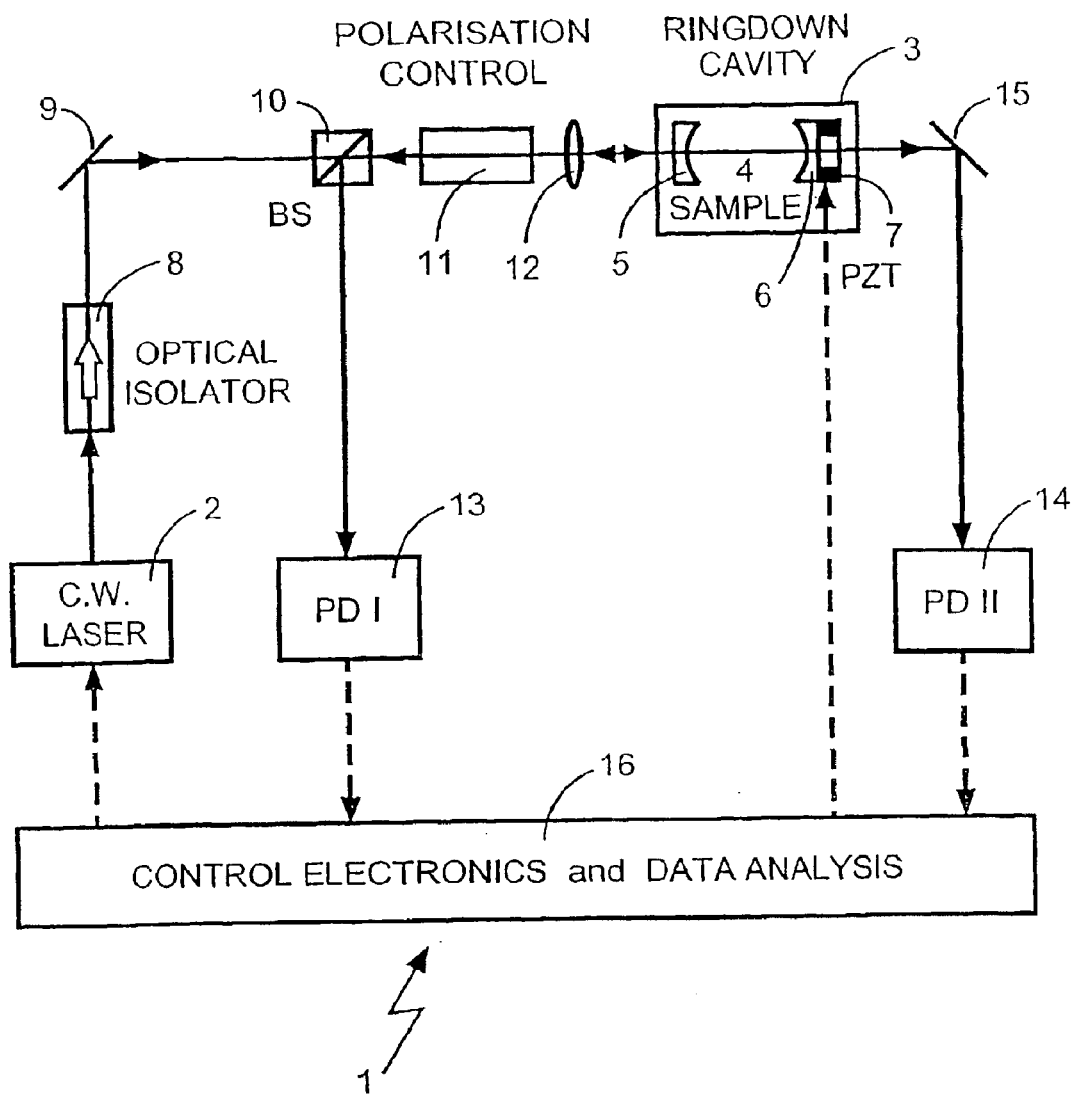
FIG. 1 is a schematic drawing of an optical apparatus according to one embodiment of the present invention.

With reference to the figures, similar apparatus features are indicated with the same reference numerals.

With reference to FIG. 1, an optical apparatus 1 in accordance with one embodiment of the present invention includes a continuous-wave laser 2 for emitting radiation at a wavelength of interest which is in optical communication with a piezoelectrically controlled ringdown cavity cell 3 containing a sample of interest 4. The ringdown cavity cell 3 respectively contains two highly reflective input and output mirrors 5 and 6, output mirror 6 being capable of being moved backwards and forwards with respect to the path of the radiation through the cell 3 by means of a piezoelectric translator 7. The optical path of the emitted radiation from the laser (shown in solid lines with arrows) is formed by an optical isolator 8, a reflector 9, a polarising beam splitter 10, a polarisation control unit 11 and a focusing lens 12. Two photodetectors 13, 14 are provided, one before the ringdown cavity cell and the other after the ringdown cavity cell. Polarisation control unit 11 enables the backwards beam to be directed efficiently to the photodetector 13 via the polarising beam splitter 10. Elements 10 and 11 also serve as an additional optical isolator for the laser 2. An alternative to elements 10 and 11 comprises a simple partially reflecting beam splitter, directing light beam to photodetector 13; this is simpler and cheaper, but it makes less efficient use of the available emitted laser radiation and provides less optical isolation than in the version shown in FIG. 1. Photodetector 14 is in optical communication with light emerging through mirror 6 via a second reflector 15. A computer 16 and suitable control electronics is also provided to control the movement of the mirror 6, the wavelength of the laser and to analyse the data detected by photodetectors 13 and 14 (electrical connections to the computer and control electronics are illustrated by dashed lines).

In use of the embodiment described in FIG. 1 radiation of a certain wavelength is emitted from the laser 2 and passed through the optical isolator 8 onto the reflector 9 where the optical path changes direction to the polarising beam spitter 10 and then to the ringdown cavity cell 3 via the polarisation control unit 11 and focal length lens 12. A portion of the emitted laser radiation then enters the cell 3 where it is multiply reflected between the mirrors 5 and 6, mirror 6 being rapidly moved backwards and forwards with respect to the optical axis by means of the piezoelectric translator 7. Ringdown radiation emerges through mirror 6 to reflector 15 and thereby to photodetector 14. Ringdown radiation also slowly emerges through mirror 5 which is combined with any emitted laser radiation which has been back-reflected off mirror 5 to the polarisation control unit 11 and then to the polarising beam splitter 10 where it changes direction and is forwarded to photodetector 13. Electronic signals are generated in the photodetectors 13 and 14 and analysed by the computer 16. By use of the apparatus of this figure optical heterodyne signals are obtained by monitoring the light that emerges through the stationary mirror 5 of the optical cavity and beating it against incident laser light reflected off that mirror. These two backward co-propagating beams combine on a square-law photodetector 13 to yield a heterodyne signal at the Doppler-shifted difference frequency. Non optical heterodyne detected cw-CRDS signals are monitored by the other photodetector 14 viewing forward-propagating light that is transmitted through the moving back optical cavity mirror 6, i.e., optical interference between radiation field $E_I$ (from reflected incident laser beam) and $E_B$ (from back transmitted intracavity optical beam) generates a heterodyne signal at photodetector 13. Photodetector 14 detects the direct forward-transmitted CRDS field $E_F$.

In use electric radiation fields $E_I$ and $E_B \exp(-t/2\tau)$ are detected by photodetector 13; these are portions of the incident laser field ($E_L$) and of the frequency-shifted light transmitted back from the optical cavity, respectively. The (relatively rapid) time dependence at optical frequencies is implicitly included in $E_I$ and $E_B$ but the (relatively slow) ringdown decay of the temporal envelope of the latter during the optical cavity sweep is shown explicitly. The signal (S) of interest is therefore of the form:

$$<S> \propto |E_I + E_B \exp(-t/2\tau)|^2 = |E_I|^2 + |E_B|^2 \exp(-t/\tau) + 2Re(E_I^* \cdot E_B) \exp(-t/2\tau)$$

The optical frequency dependence of each of these fields is time-averaged by photodetector 13 but the Doppler-induced frequency difference between $E_I$ and $E_B$ allows their cross term ($E_I^* \cdot E_B$) to appear as an optical heterodyne signal containing a slowly varying exponential decay factor that depends on the optical cavity ringdown time $\tau$. More rapidly varying oscillations associated with the ($E_I^* \cdot E_B$) heterodyne cross term are not shown explicitly in equation 2. The term in $|E_B|^2$ is comparable to the direct cw-CRDS signal proportional to the electric radiation field $|E_F|^2$ that is processed by photodetector 14. The optical heterodyne detected signal monitored by photodetector 13 has an advantage in that the field $E_I$ is much stronger than $E_B$ or $E_F$ resulting in a significant amplification factor. Moreover the optical heterodyne detected signal monitored by photodetector 13 decays twice as slowly as the direct (photodetector 14 detected) ringdown signal which further enhances detection sensitivity. The higher frequency domain of the optical heterodyne detected signal facilitates reduction of low-frequency technical noise by high-pass filtering. Accordingly there is no need for a separate optical sideband generator or local oscillator.

Figure 2:
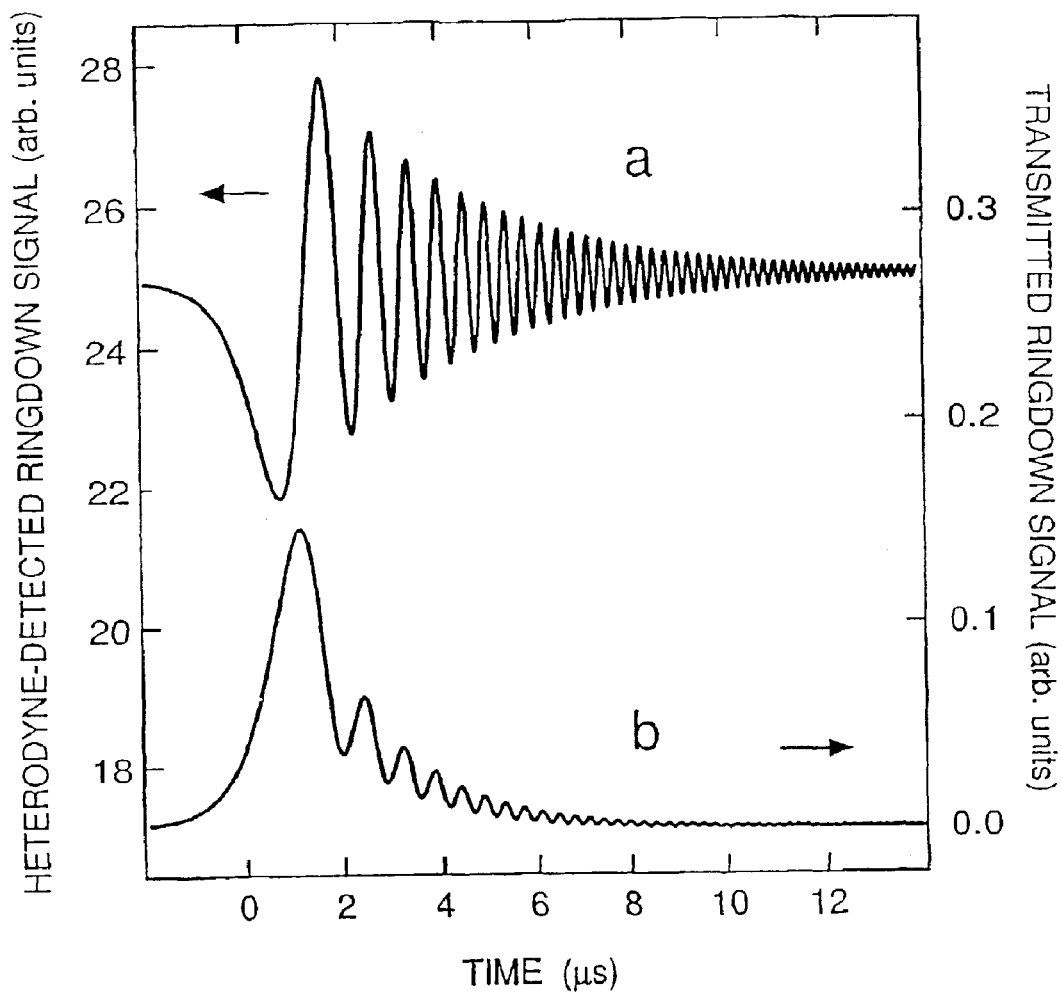
FIG. 2 (trace a) is a graph of the predicted optical heterodyne build-up and ringdown signal versus time using the optical apparatus of FIG. 1 when compared with the transmitted build-up and ringdown signal (trace b) predicted using the same swept-optical cavity ringdown apparatus in the absence of optical heterodyne detection.
Figure 3:
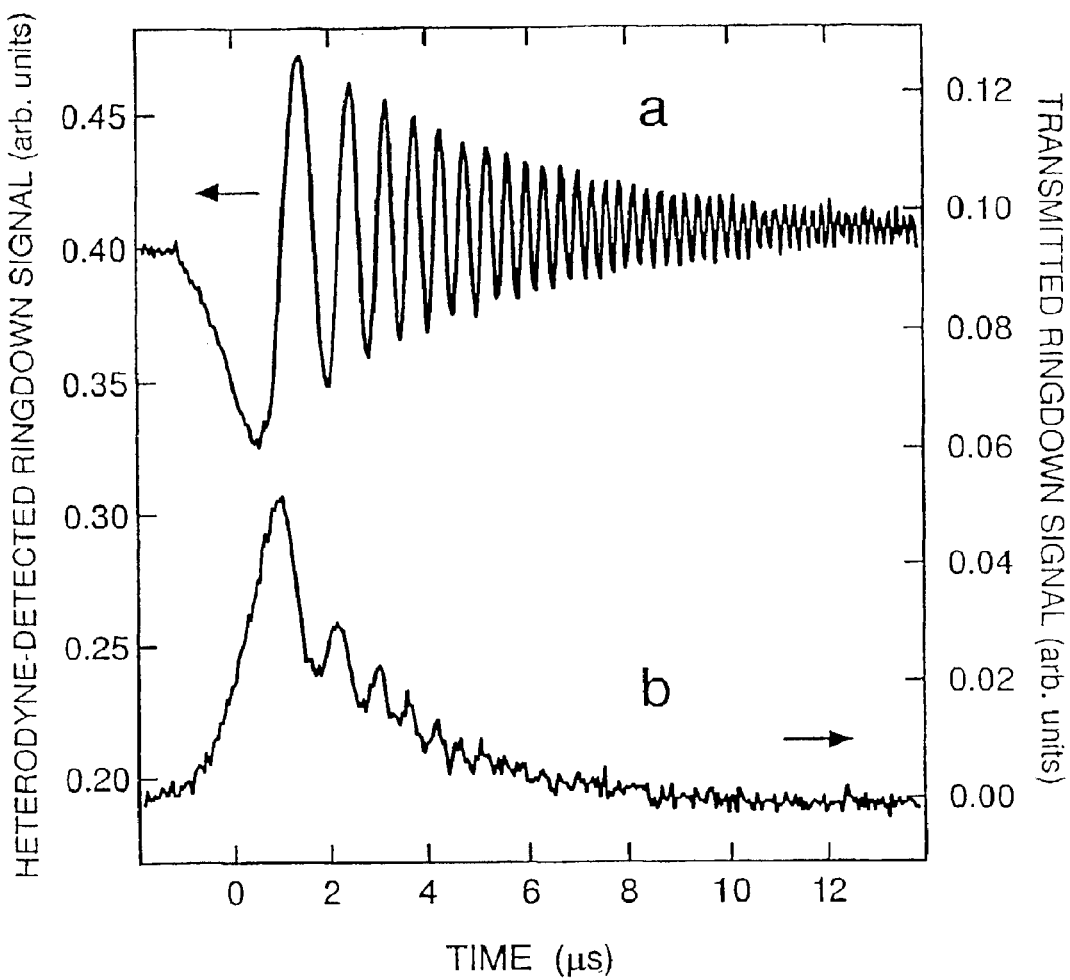
FIG. 3 (trace a) is a graph of the actual optical heterodyne build-up and ringdown signal versus time measured using the optical apparatus of FIG. 1 when compared with the transmitted build-up and ringdown signal (trace b) measured using the same swept-cavity ringdown apparatus in the absence of optical heterodyne detection.
Figure 4:
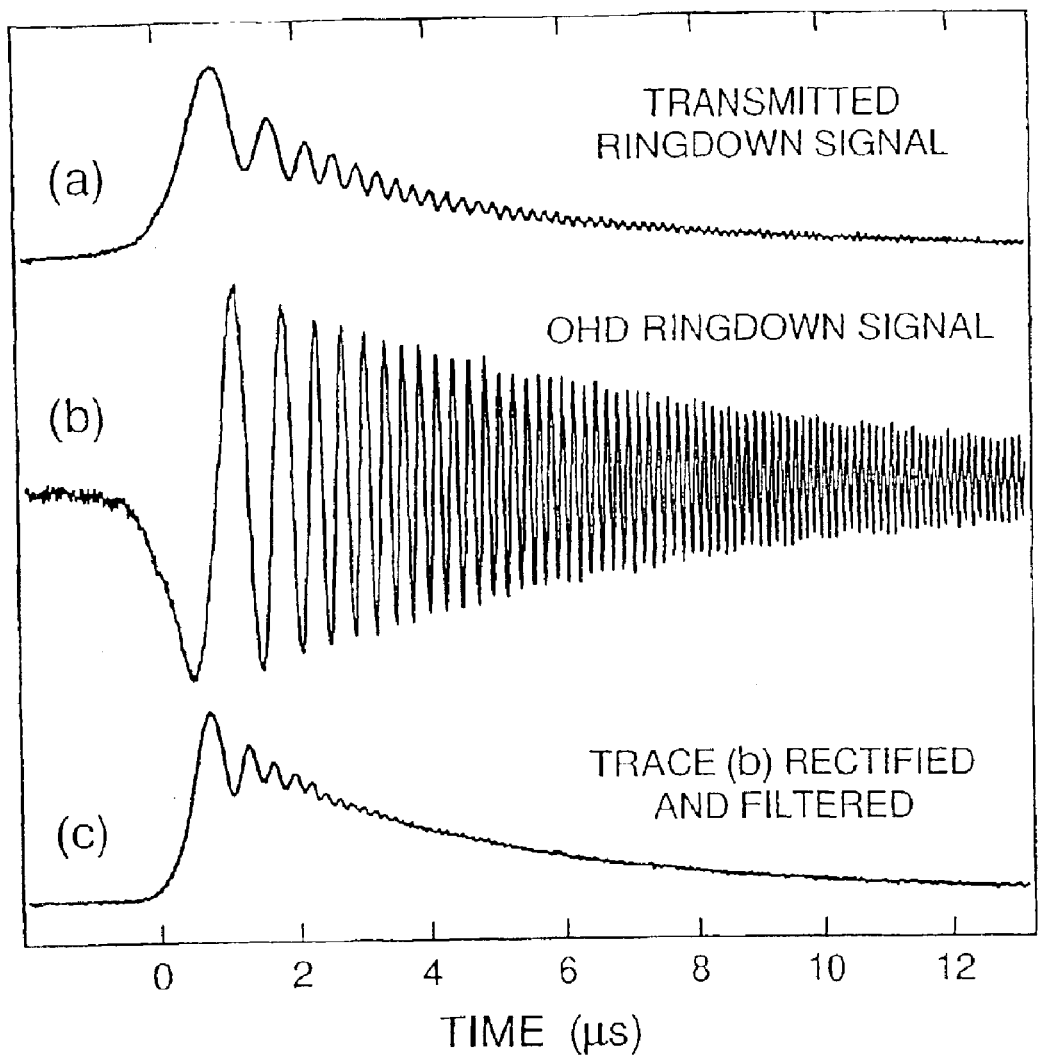
FIG. 4 is a graph of simultaneously recorded cw-CRDS build-up and ringdown signals measured with a rapidly swept optical cavity (a) and optical heterodyne detection (b, c)

FIGS. 2, 3 and 4 present relevant results. The results of using the apparatus of FIG. 1 are shown in FIG. 3 line a, the predicted results using numerical simulation is shown in FIG. 2 line a. Ringdown times are evaluated from the envelope of transmitted intensity profiles. The predicted results were mathematically simulated by use of multiply reflected laser beams and updating the amplitude and phase at each round-trip time taking into account the Doppler-type frequency shifts which occur each time a beam is reflected from the moving mirror and the changing round trip time inside the optical cavity. Line a in each of FIGS. 2 and 3 represents the optical heterodyne signal registered by photodetector 13 in FIG. 1; line a oscillates at the difference frequency between the originally emitted laser radiation and the frequency-shifted optical cavity ringdown radiation. For comparison in both Figures, line b shows the results obtained and those predicted when using a rapidly swept optical cavity cell but in the absence of optical heterodyne detection. Line b in each of FIGS. 2 and 3 is as registered by photodetector 14 in FIG. 1; line b shows that the intensity of the transmitted light increases steadily to a maximum, then as the optical cavity moves from resonance to non-resonance, oscillations set in, the period and depth of modulation decreasing as time delay increases. The ringing tends to be smoothed out by finite optical bandwidth of the input laser light, since each of its frequency components resonates with the optical cavity at a slightly different delay. The later part of the decay optical transmission curve becomes smooth and is well fit by a single-exponential decay function enabling the ringdown time to be evaluated reliably.

A comparison of the results of optical heterodyne detection (line a in FIGS. 2 and 3) when compared with that of transmitted detection (line b in FIGS. 2 and 3) and as mentioned above shows that the method of the present invention is more sensitive, with significant gains in signal-to-noise ratio, than a prior art method using a rapidly swept optical cavity in the absence of optical heterodyne detection. The optical heterodyne signal also decays more slowly than the directly detected ringdown signal by a factor of two and this also enhances detection sensitivity.

FIG. 4 similarly shows a comparison of optical heterodyne detection with cw-CRDS using a rapidly swept optical cavity in the absence of heterodyne detection. The forward-transmitted signal from photodetector 14 (line a) builds up and peaks just after the exact resonance point (at t=0 on the abscissa) between the optical cavity and the laser wavelength. The optical cavity then moves out of resonance and oscillations set in with their period and depth of modulation decreasing as time delay increases. The decay envelope depends on the energy loss rate of the optical cavity and can be used for CRDS measurements. The optical heterodyne detected ringdown signal (line b) contains information about the amplitudes and relative phase of the optical field $E_I$ and $E_B$ that are monitored by photodetector 13 at the Doppler-shifted difference frequency. For useful optical heterodyne detected cw-CRDS measurements it is desirable to extract the ringdown decay rate $\tau^{-1}$ from the signal of photodetector 13. One possible approach would be to fit features of optical heterodyne detected waveforms such as shown in line b to a model-derived function. A more efficient method capable of implementation in real time while an optical absorption spectrum is being recorded entails preprocessing signals from photodetector 13 by analog electric circuits that rectify and smooth the oscillatory part of the ringdown decay using a multiplier and low-pass filter. The latter has been used in line c yielding a smooth, single-exponential decay curve from which the ringdown time $\tau$ can be rapidly and accurately derived.

Figure 5:
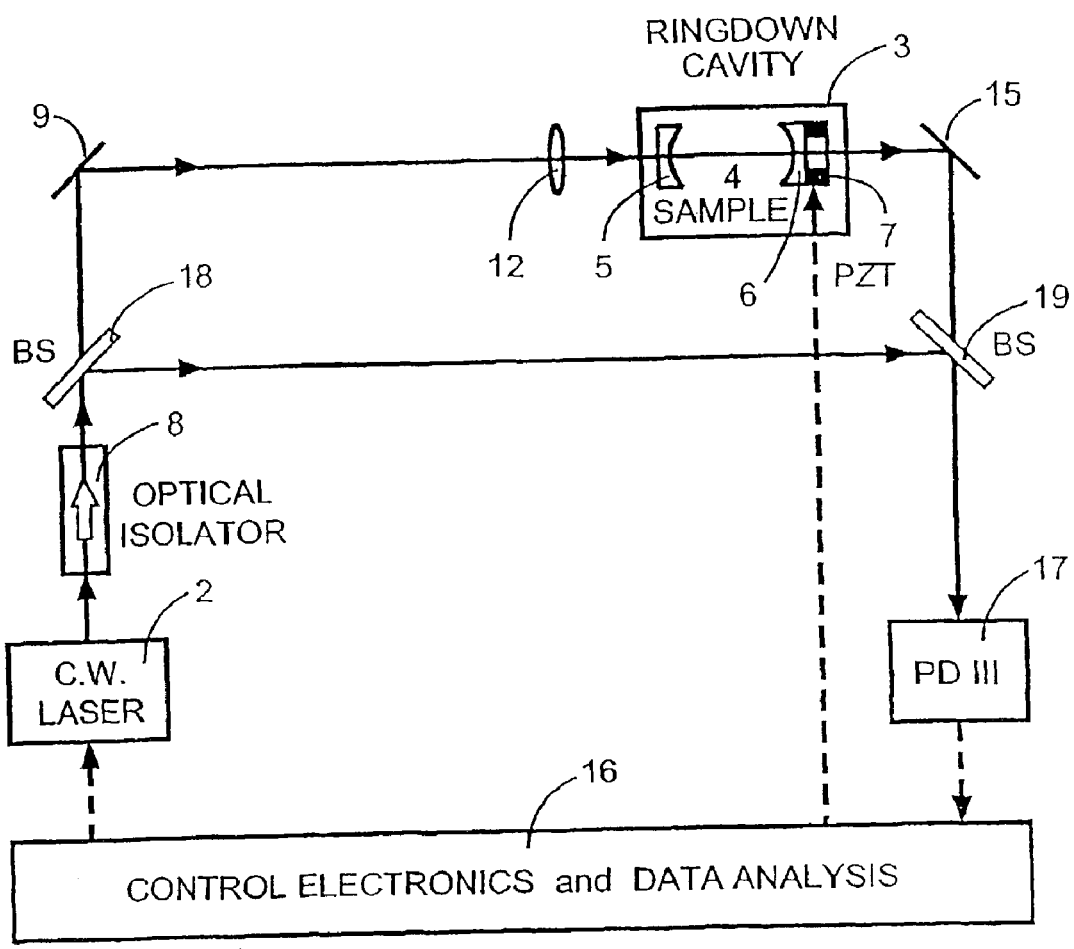
FIG. 5 is a schematic drawing of an optical apparatus according to another embodiment of the present invention.

FIG. 5 shows an alternative embodiment to that shown in FIG. 1. Similar apparatus features are given the same reference numerals. This apparatus differs from that shown in FIG. 1 by the use of a single photodetector 17 and the fact that either of the mirrors 5, 6 can be moved (although in this drawing only mirror 6 is shown as being capable of being moved). Beam splitter 10, polarisation control unit 11 and photodetector 13 which appear in FIG. 1 are not needed in this embodiment. Additional beam splitter 18 directs a portion of emitted laser radiation along a second optical path to a second beam splitter 19, where it is combined with ringdown radiation emerging from the mirror 6 and forwarded by reflector 15 to the photodetector 17. For applications using high output energy lasers this embodiment is a good choice due to its simplicity. However this embodiment is less desirable than that of the first embodiment shown in FIG. 1 owing to less efficient use of available laser output energy.

EXAMPLE 1

The rovibrational optical absorption band of carbon dioxide gas ($CO_2$) at ~1.53 μm was examined spectroscopically using the optical-heterodyne detection continuous wave CRDS method of the present invention with a rapidly swept optical cavity and using the apparatus shown in FIG. 1. The apparatus used included a cw TDL tunable diode laser (New Focus model 6262/6200; ~5 mW single-mode output; tunable over 1.50–1.59 μm with ~1-MHz optical bandwidth), a piezoelectrically controlled ringdown optical cavity, two amplified photodetectors 13 and 14 (InGaAs; 125-MHz bandwidth), a digital oscilloscope (Tektronix TDS3054; 500-MHz bandwidth), and control electronics with IEEE-488 computer interface. The TDL beam traversed an optical isolator (−80 dB) and was mode-matched to the ringdown cavity by a lens of 50-cm focal-length. A polarisation control unit (a 45° Faraday rotator which also augmented optical isolation) enabled a polarising beam splitter (PBS) to direct the backward-propagating light fields $E_I$ and $E_B$ to the photodetector 13. The configuration thereby made efficient use of available laser power for optical heterodyne detection measurements. The incident TDL optical power was attenuated to ~35 μW to avoid saturation of the very sensitive low-noise preamplifier associated with photodetector 13. Photodetector 14 monitored the direct CRDS signal forward-transmitted by the ringdown cavity, which comprised two concave mirrors (>99.96% reflectivity, ~1-m radius, 45 cm apart) mounted in an evacuable optical cell fitted with electronic manometers. A cylindrical low-voltage PZT (driven by ramp with ~10-V amplitude) allowed the ringdown optical cavity length to be swept with amplitude of ~1.6 μm at frequencies up to ~1 kHz. A synchronous gate selected the portion of signal output from 13 and/or 14 around the midpoint of each positive-going sweep, where the velocity of the optical cavity mirror was constant (typically ~1 mm s$^{-1}$). The digital oscilloscope was level-triggered by the ringdown signal, since optical cavity resonances occurred at points in the sweep cycle that varied as the input TDL wavelength was scanned. Successive ringdown curves were collected at a rate of ~500 Hz and averaged in the oscilloscope, with a dead time for each real-time averaging and fitting operation of ~0.1 s during which a ringdown time τ was extracted instantaneously from rectified and filtered modification of the averaged waveform (typically over the range 5<τ<15 μs) by computer fitting and the TDL wavelength was incremented (in steps of ~0.01 nm for a coarse scan or ~0.4 pm for a fine scan) thereby generating a CRD spectrum.

Figure 6:
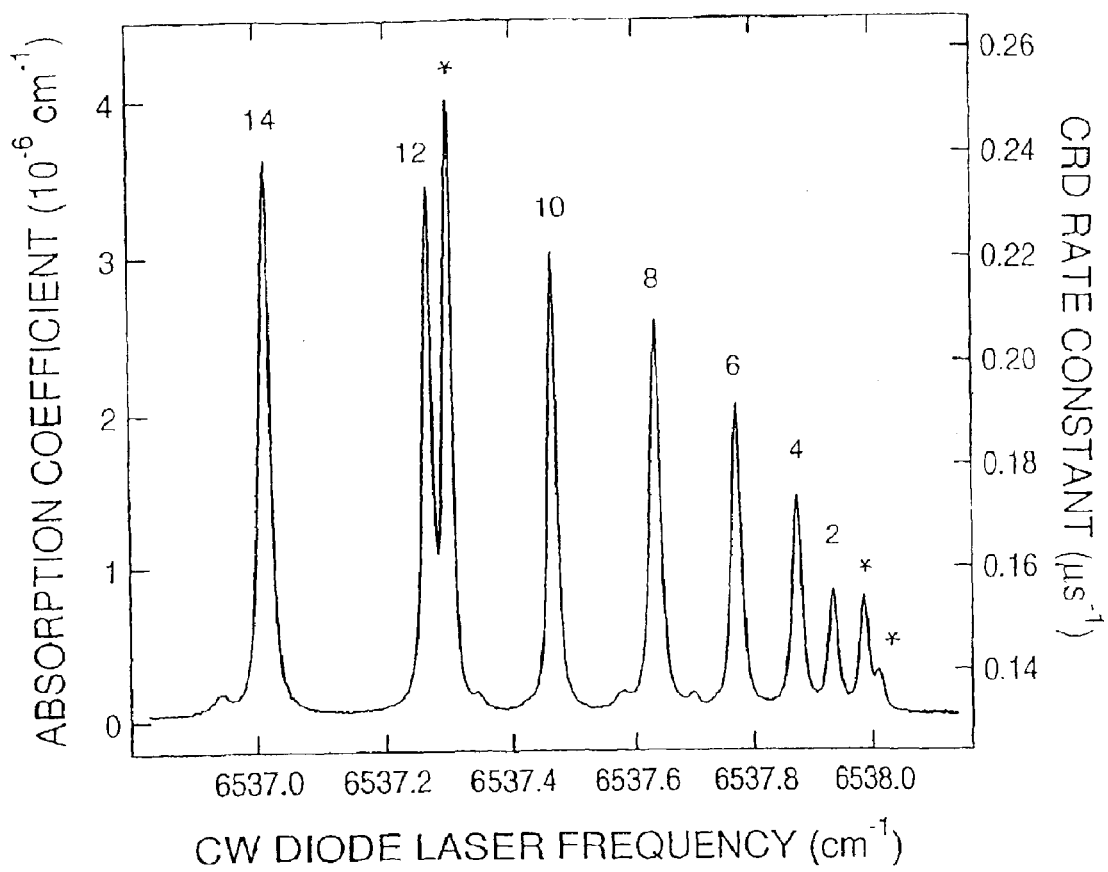
FIG. 6 is a cw-CRDS scan of a weak optical absorption band of $CO_2$ obtained by use of the method and apparatus of the present invention.

The $CO_2$ band in the vicinity of 1.53 μm is extremely weak and is difficult to detect by conventional infrared spectroscopy (even in a long-path optical absorption call). FIG. 6 shows a cw-CRDS trace recorded for $CO_2$ at 50 mbar and 296 K. At each wavelength step, 256 build-up-and-decay curves were averaged by the digital oscilloscope and the decay rate averaged a further eight times by computer; this required a dwell time of ~5 s for each 50-MHz (0.017-cm$^{-1}$) step in the finely scanned spectrum. Prominent features of the spectrum are labelled with corresponding rotational quantum numbers J, belonging to the Q branch of the 6538-cm$^{-1}$ ($11^12$)$_{II}$–$00^00$ rovibrational optical absorption band. Other peaks (asterisked) belong to three other bands in the same spectral region. Even weaker (unlabelled) features are thought not to have been previously observed and are tentatively attributed to isotopic species of $CO_2$ (e.g. $^{13}CO_2$) and/or ultra-weak hot bands. FIG. 6 was recorded with the incident TDL optical power attenuated 100-fold to ~35 μW to avoid saturation of the very sensitive low-noise preamplifier associated with photodetector 13. From the observations a noise-limited sensitivity for optical absorbance or optical absorption coefficient detection of 3×10$^{-9}$ cm$^{-1}$ which corresponds to a minimum detectable $CO_2$ partial pressure of 37 μbar for the most intense feature (peak* at 6537.3 cm$^{-1}$) provided that the total sample pressure is low enough to maintain Doppler-limited linewidths (0.012 cm$^{-1}$ FWHM). Where this is not the case, pressure broadening may be required as there is a linear pressure dependence of linewidth at low pressure (resulting in a Doppler limit). An estimated dynamic range (over which linear signal detection is possible, depending on factors such as the noise level and linear amplification range of the photodetector and its preamplifier) of at least 35 dB (i.e., a factor of 3×10$^3$) was deduced. These performance figures are markedly superior to those obtained (7×10$^{-8}$ cm$^{-1}$ and ~20 dB) in previous CRDS measurements with cw and pulsed lasers.

The above form of CRDS sensitivity, measured as optical absorption per unit length (e.g., cm$^{-1}$ units), is useful as an absolute performance measure, but it is useful to relate it to a minimum detection limit (MDL) based on concentration or pressure, or to a mixing ratio (e.g., ppm or ppb units). Such MDLs depend on the particular sample conditions and spectral feature examined. For instance, the following discussion explicitly considers trace detection of $CO_2$ in air.

The noise-limited sensitivity obtained in FIG. 6 (3×10$^{-9}$ cm$^{-1}$) corresponds to a minimum detectable $CO_2$ partial pressure of 37 μbar for the most intense feature (asterisked at 6537.3 cm$^{-1}$), provided that the total sample pressure is low enough to maintain Doppler-limited linewidths (0.012 cm$^{-1}$ FWHM). For gas samples measured at atmospheric pressure (e.g., by dilution in air), pressure broadening needs to be considered in addition to Doppler broadening. This effectively degrades the minimum pressure at which a dilute species can be detected because peak heights are reduced and overlapping of spectral lines is increased (by a factor of ~14 between 50 mbar and 1 bar).

The result discussed above applies to the relatively weak R(50) transition (asterisked at 6537.3 cm$^{-1}$ in FIG. 6) of the 1.54-μm ($30^01$)$_I$–($00^00$) band; the most intense peaks in the same band (e.g., R(14) at 6514.25 cm$^{-1}$) are ~29 times stronger and would therefore enable a minimum $CO_2$ pressure of ~1.3 μbar to be detected by the same optical heterodyne cw-CRDS approach. For a sample of $CO_2$ diluted in air to a total pressure of 50 mbar (above which pressure broadening becomes dominant over Doppler broadening), this would correspond to a MDL of ~26 ppm; the corresponding MDL for $CO_2$ in air at 1 bar would be ~18 ppm, after allowing for pressure broadening. Lower MDLs (~2 ppm in air at 1 bar) should be attainable by tuning to the nearby 1.57-$\mu$m $(30^01)_{II}$–$(00^00)$ band which is ~8 times more intense than the 1.54-$\mu$m $(30^01)_I$–$(00^00)$ band that is studied in the preceding example, as represented by FIG. 6.

Such projected optical detection limits, for optical heterodyne cw-CRDS spectroscopy in weak combination bands, are attained with relatively inexpensive 1.55-$\mu$m telecommunication-band instruments and components. The fundamental optical absorption bands of $CO_2$, namely, $(00^01)$–$(00^00)$ at ~4.2 $\mu$m and $(01^10)$–$(00^00)$ at ~15.0 $\mu$m, have vibrational band strengths that are respectively $1.6 \times 10^6$ and $1.4 \times 10^5$ times greater than for the 1.54 $\mu$m $(30^01)_I$–$(00^00)$ combination band that is of primary interest here (e.g., in FIG. 6). Sub-ppb sensitivity for $CO_2$ in air is attainable in the 4.2-$\mu$m $\nu_3$ fundamental optical absorption region by fourier-transform infrared (FTIR) spectroscopy in a high-throughput multipass absorption cell. CRDS-based detection of $CO_2$ in air is likewise expected to have particularly high sensitivity in the 4.2-$\mu$m and 15.0-$\mu$m fundamental optical absorption regions, compared to combination bands in the vicinity of 1.55 $\mu$m. However, this would require substantial (costly) changes in laser wavelength, ringdown cavity mirrors, photodetector, and other optical elements.

Figure 7:
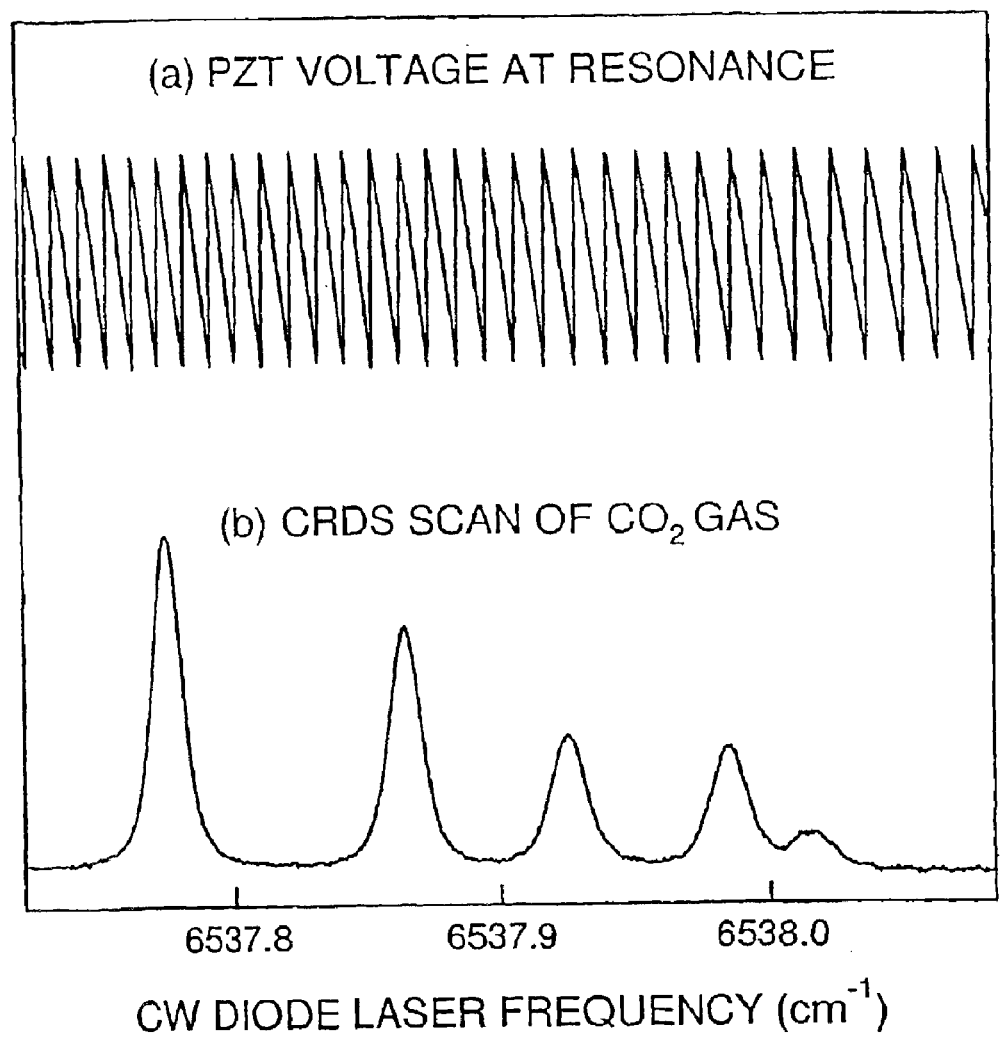
FIG. 7 is a cw-CRDS scan (trace a) similar to that in FIG. 6 and a simultaneously recorded wavelength-calibration trace (b) comprising the PZT voltage at which the build-up and ringdown signal transient triggers the digital oscilloscope in the control electronics, to register any irregularity or nonlinearity of the cw laser wavelength scan.

Another cw-CRDS scan of a portion of the same spectrum of $CO_2$ gas as in FIG. 6 is presented with even higher definition in trace (b) of FIG. 7. Above it, a simultaneously recorded wavelength-calibration trace (a) registers deviations from nonlinearity of the cw laser scan. This wavelength-calibration trace is obtained by recording the voltage that is applied to the PZT optical cavity-length controller at the instant at which the leading edge of the build-up and ringdown signal transient triggers the digital oscilloscope in the control electronics. The ringdown cavity thereby serves conveniently as an automatic reference etalon, as well as performing its primary spectroscopic function. This feature enables the resonance point of a remotely located, rapidly swept ringdown cavity to be calibrated simply as the input wavelength of the cw laser is slowly scanned, avoiding extra components usually needed to generate wavelength markers and calibrate wavelength-scan nonlinearities.

PARTICULAR INSTRUMENTAL ADVANTAGES

It will be appreciated by those skilled in the art that the invention can be embodied in other forms. For example it may be possible to use a lower-gain, low-noise photodetector to take advantage of the full 5 mW power of the tuning diode laser, to replace the continuous optical cavity-scan scheme with a more abrupt mirror displacement of well-defined amplitude that would shift the effective optical heterodyne detected difference frequency further above that of low-frequency technical noise, to use optical-fibre coupling to allow the ringdown cavity to be remotely located relative to the tuning diode laser and detection system, thereby facilitating industrial, medical, agricultural and environmental sensing applications.

Figure 8:
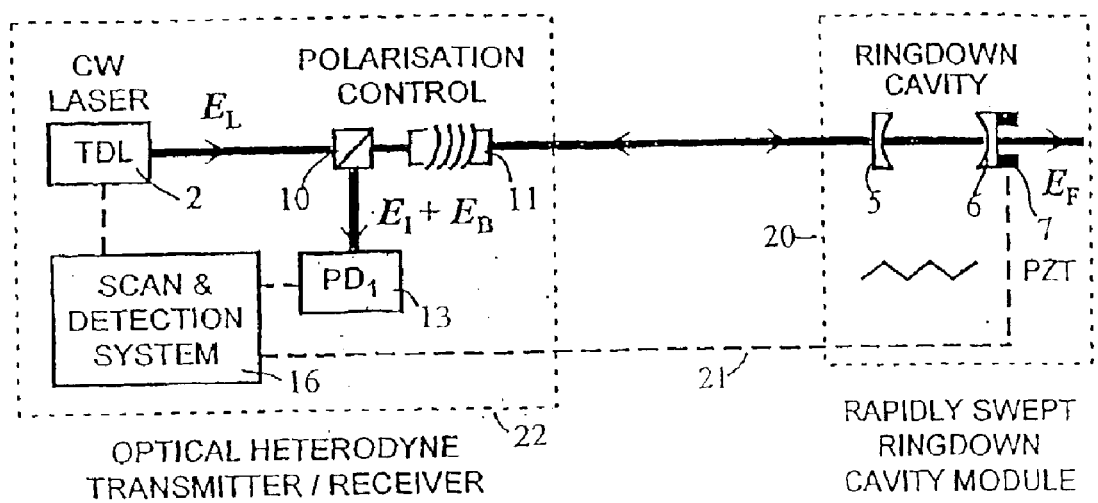
FIG. 8 is a schematic drawing of a single-ended embodiment of the swept-cavity ringdown apparatus in a form suitable for semi-remote sensing with optical heterodyne detection.

A major advantage of the cw-CRDS apparatus with a rapidly swept optical cavity and optical heterodyne detection is that the signal to be detected returns to the optical transmitter/receiver apparatus by counter-propagating along the same path as that of the incident laser beam, thereby enabling single-ended detection. FIG. 8 presents a further schematic representation of the same embodiment of the swept-optical cavity ringdown apparatus as already shown in FIG. 5. The cw laser 2 is typically a single-longitudinal-mode tunable diode laser (TDL) and the optical detector is typically a photodiode ($PD_1$; equivalent to component 13, labelled PD1 in FIG. 1). The optical field amplitudes ($E_L$, $E_F$, $E_I$ and $E_B$) defined in the context of equation (2) are shown explicitly in FIG. 8. This representation emphasises the single-ended detection prospects for the optical heterodyne cw-CRDS apparatus, with the ringdown cavity module 20 (on the right-hand side of FIG. 8) able to be remotely located relative to most of the detection system 22 (on the left-hand side of FIG. 8) and coupled to it solely by the laser beam and an electrical cable 21 carrying the optical cavity-sweep voltage to the PZT element 7 (depicted as a sawtooth waveform in FIG. 8). An optical detector (component 14, labelled PDII in FIG. 1) of the forward-transmitted light field $E_F$ is superfluous in such a single-ended detection embodiment; it has therefore been omitted from FIG. 8. Nevertheless, such a secondary detector can be useful for preliminary alignment and optimisation of the cw-CRDS apparatus. In cases where a second optical detector (14) is not needed to monitor forward-transmitted light, it is possible for the moving back mirror 6 of the ringdown cavity to be a total reflector and thereby enhance the amplitude of backward-propagating optical heterodyne signal.

Figure 9:
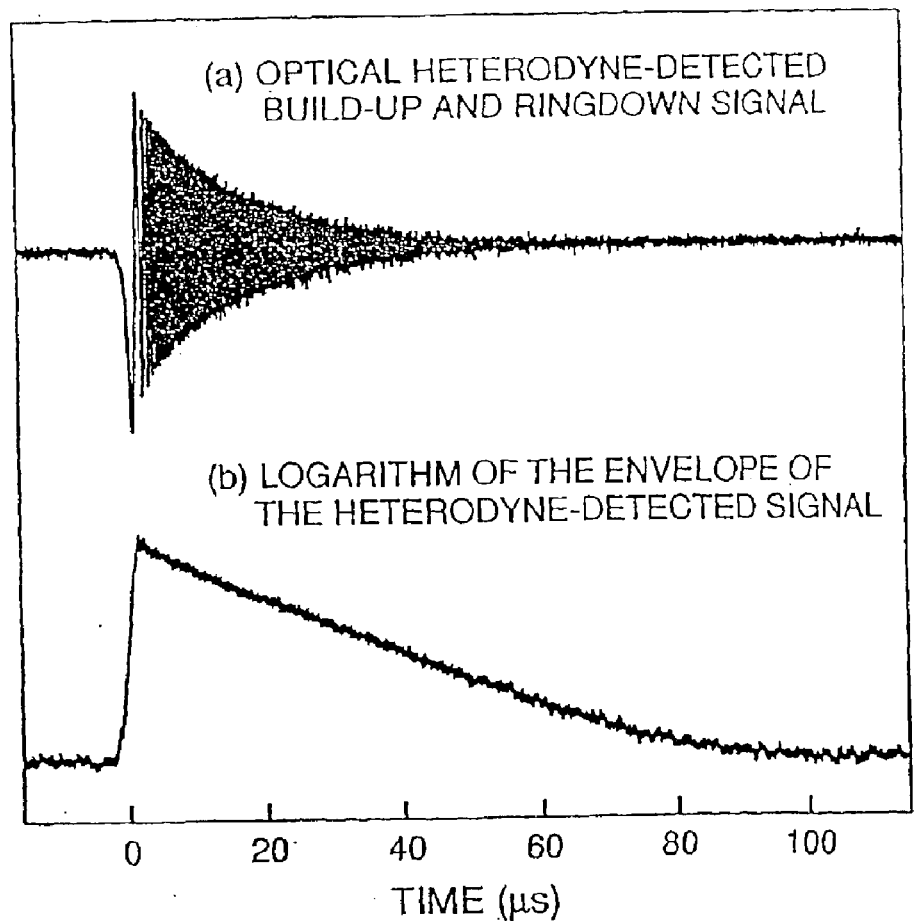
FIG. 9 is a graph of simultaneously recorded cw-CRDS build-up and ringdown signals with a rapidly swept optical cavity and optical heterodyne detection, either unprocessed (trace a) as in FIG. 4(b) or processed by a commercially available demodulating logarithmic amplifier (trace b)

Another mode of operation, with a rapidly swept optical cavity and optical heterodyne detection, is demonstrated in FIG. 9. This presents simultaneously recorded cw-CRDS signals, either unprocessed (trace a) as in FIG. 4(b) or processed (trace b) by a commercially available demodulating logarithmic amplifier (Analog Devices model AD8307, bandwidth DC-500-MHz, linearity ±1 dB, dynamic range 92 dB). The latter approach directly converts the exponentially decaying full-wave envelope of optical heterodyne oscillations, as depicted in trace (a), into a smooth linear decay, the slope of which provides a means of measuring the ringdown time ($\tau$). This is more convenient than the rectify-and-smooth method, previously used in the context of FIG. 4 to generate an exponential decay curve (trace c) from the full-wave envelope (trace b). Moreover, the use of a demodulating logarithmic amplifier, as in FIG. 9(b), advantageously preserves the two-fold slower decay rate $(2\tau)^{-1}$ of the full-wave envelope in FIGS. 4(b) and 9(a), relative to the rectified decay rate $\tau^{-1}$ of FIG. 4(c).

Figure 10:
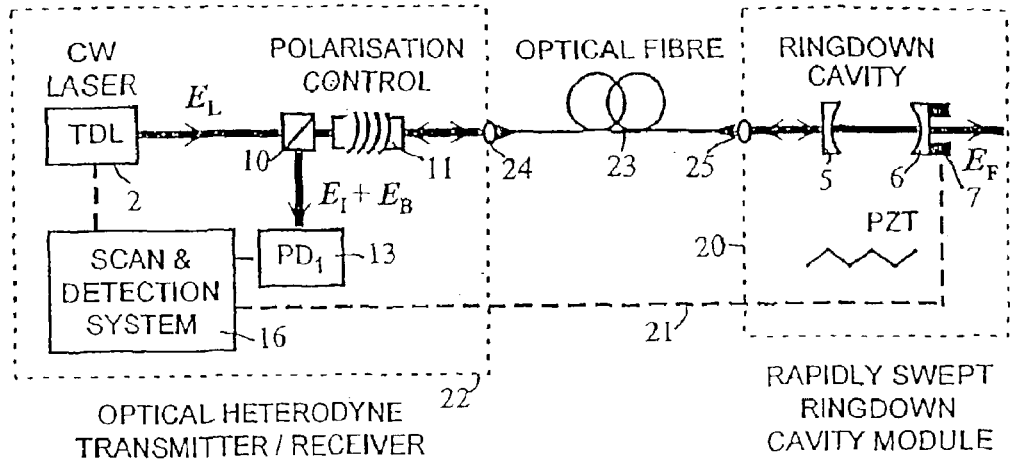
FIG. 10 is a schematic drawing of a single-ended embodiment of the swept-optical cavity ringdown apparatus similar to that in FIG. 8, with a single-mode optical fibre used both to deliver laser light to the ringdown cavity and to collect reflected light for optical heterodyne detection. A mechanical fibre-polarisation manipulator (not explicitly shown in the drawing) is also needed to preserve the polarisation of the light that the fibre transmits in both directions.

As indicated above, the invention is amenable to embodiments in which optical fibres are used to transmit the radiation over various portions of the beam path. Standard optical fibres are typically optimised for working in individual wavelength ranges (e.g. 1.5 to 1.8 microns). Such optical fibres optimised for one wavelength can however still be used for longer wavelengths with single-mode characteristics (the fibre thereby becoming multi-mode operable below its "cut-off" wavelength). Accordingly it is possible for optical fibres to cover the complete spectral range from visible to the near infrared. One embodiment in which optical fibres are used is illustrated in FIG. 10, in which a single-mode optical fibre 23 is used to transmit the cw laser beam from the (left-hand) optical heterodyne transmitter/receiver section 22 of the apparatus to the (right-hand) ringdown cavity module 20 via microscope objective lenses 24 and 25, which can be remotely located and connected to the main instrumental control system solely by the optical fibre 23 carrying the laser beam and an electrical cable 21 carrying the optical cavity-sweep voltage to the PZT element 7. A mechanical fibre-polarisation manipulator (not explicitly shown in the FIG. 10) is typically needed to adjust the polarisation of the light that the fibre transmits in both directions. It is important to be able to control the polarisation of the forward-propagating light entering the ringdown cavity module 20 and of the backward-propagating light returning to the optical heterodyne receiver 22. An alternative embodiment of this apparatus could locate the PZT voltage supply close to the ringdown cavity and transmit control signals to and from the optical heterodyne transmitter/receiver instruments by another optical fibre or by wireless means. Either way, these embodiments yield a single-ended cw-CRDS optical detection system, in which the relatively inexpensive, rugged ringdown cavity section can be widely separated from the more sensitive, expensive main instrumental control system. Experimental cw-CRDS results, such as those presented in FIGS. 7 and 9, have been successfully recorded with light transmission by optical fibre in this way. It is critical to ensure efficient coupling into the single-mode optical fibre of both the incident laser light and the counter-propagating light reflected from the rapidly-swept ringdown optical cavity, but such techniques are routinely used by those skilled in the art.

A further extension of this approach to optical heterodyne cw-CRDS using optical fibre coupling comprises an embodiment in which there is a single, central instrumental control system (including the optical heterodyne transmitter/receiver section of the apparatus and a single optical detector $PD_1$) and numerous rapidly-swept ringdown cavities, each coupled by a single-mode optical fibre and PZT control link to the central instrumental system. A suitable optical fibre splitter or switch module can be used to distribute the laser and return ringdown light to and from different locations of a site at which the various ringdown cavities are positioned. This approach enables the more expensive, less rugged components of the overall apparatus to be positioned in a central secure location (e.g., in an air-conditioned control room) while less expensive, more robust ringdown cavities are multiply distributed in more hostile and/or less accessible locations (eg., at various gas effluent sources on an industrial, environmental or agricultural site or in a series of wards in a hospital). In some applications, it is advantageous to use a vacuum pump to direct the sampled gas through a suitable particle filter into a sealed ringdown cavity where the spectroscopic measurements are made at sub-atmospheric sample pressure to minimise pressure broadening of optical absorption lines and thereby increase the specificity of detection.

Figure 11:
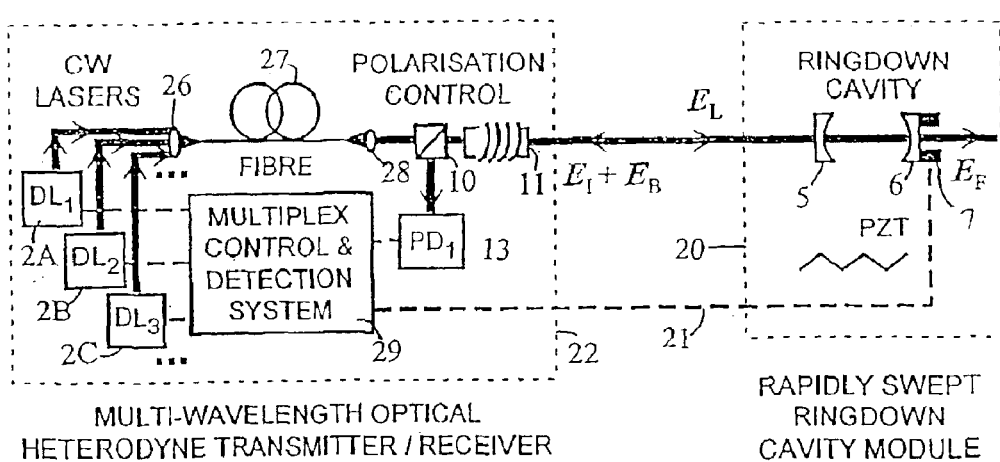
FIG. 11 is a schematic drawing of a single-ended, multiplex embodiment of the swept-cavity ringdown apparatus similar to that in FIGS. 8 and 10, with several separate tunable cw laser beams combined in a single-mode optical fibre and simultaneously coupled into the ringdown cavity such that each preset laser wavelength resonates at a different point in the optical cavity-length sweep cycle. A mechanical fibre-polarisation manipulator (not explicitly shown in the drawing) is also needed to preserve the polarisation of the light that the fibre transmits.

Another optical fibre-based embodiment of the optical heterodyne cw-CRDS invention concerns the use of more than one cw laser wavelength for multiplex spectroscopic characterisation. FIG. 11 depicts an embodiment of this type, with beams from several cw lasers ($DL_1$, $DL_2$, $DL_3$, ... ; 2A, 2B, 2C, ... ) each having a different wavelength combined spatially, directionally and with preserved polarisation. This is achieved by coupling each laser beam, by means of either beam-steering reflectors (mirrors or prisms) or by suitable beam splitters, into a short length of single-mode optical fibre, by techniques that are routinely used by those skilled in the art. As shown in FIG. 11 single mode coherent radiation from each diode laser 2A, 2B and 2C is directed simultaneously by a microscope objective lens 26 into one end of an optical fibre 27. The light emerging from the other end of the optical fibre 27 is collected by a second microscope objective lens 28 such that all beams of light from the several continuous-wave lasers are co-aligned, propagating with common spatial characteristics. From the second microscope objective lens 28, the light is then forwarded through a beam splitter 10 and polarisation control unit 11 and then into the ringdown cavity cell such as already described with respect to FIG. 1.

The lasers used ($DL_1$, $DL_2$, $DL_3$, ... ; 2A, 2B, 2C, ... ) are suitably chosen such that the frequency differences among them are much larger than the bandwidth of the response frequency of the photodetector 13 $PD_1$) as signals at different frequencies can disturb the cw CRDS signals. The co-alignment of the different laser beams is necessary to ensure that all can be coupled efficiently into the one ringdown optical cavity. The polarisation orientation of each of the cw laser beams emerging from the fibre 23 typically needs to be adjusted by using a mechanical optical fibre polarisation manipulator or by other means known to those skilled in the art. Each cw laser is set to emit at a particular characteristic wavelength. Some of these wavelengths are chosen to be resonant with spectroscopic features of gas-phase chemical species that are of particular interest. At least one other wavelength is chosen such that it is removed from any known spectroscopic features, in order to measure the non-resonant background or baseline. The ringdown cavity is rapidly swept in the manner of previously described embodiments of the invention. Chemical species that are typically of interest usually have many characteristic optical absorption features within a narrow wavelength range. This provides flexibility in the setting of laser wavelengths. The length of the ringdown cavity at rest is an additional adjustable parameter. Laser wavelengths and the optical cavity length can be precisely set to ensure that the build-up and ringdown transient for each of the different wavelengths (from cw lasers $DL_1$, $DL_2$, $DL_3$, ... ) will occur at a different point in the optical cavity-sweep cycle. Each of these build-up and ringdown transients must be clearly separated (e.g., by a few cavity ringdown time intervals) from any other transient to avoid unwanted interference effects. It is then possible to collect cw-CRDS signals for several (e.g., 2–8) characteristic spectroscopic features for different absorbing species and non-resonant background reference points, all within a single rapid sweep period (typically 1 ms) of the ringdown optical cavity. The optical reflectivity of the cavity reflectors (such that increased reflectivity causes the empty-cavity ringdown time to increase) imposes a limit on the number of build up and decay transients that can be accommodated within a particular optical cavity sweep period. This results in a trade off between sensitivity (enhanced by high reflectivity), data collection rate (limited by the cavity sweep rate) and the number of wavelengths that can simultaneously be monitored. A multiplex control and detection system 29 (suitably a DFB-distributed feedback-laser) is also provided. The multiplexer 29 controls current and temperature of each laser so that they provide correct wavelengths (no timing needed) and also controls scan rate and amplitude of voltage of the piezo-electric translator such that the optical build up of each resonance point occurs at a different point in the cavity sweep cycle and also pre-adjusts the rest length of the cavity. A reference cell and/or wavelength meter can also be included to check wavelength. Such multiplex cw-CRDS detection using a rapidly swept optical cavity and optical heterodyne detection is effectively simultaneous on the time scale of many gas-phase processes of interest. In many applications (e.g., with a static sample in the optical cavity), the time scale of fluctuations of the absorbing medium is long relative to the optical cavity sweep period and the successive multiplex build up and decay transients that are accommodated within that period; it is then possible to average over successive cavity sweeps to enhance the signal-to-noise ratio and CRDS sensitivity. In other applications, (e.g., with a turbulent or rapidly reacting sample in the optical cavity), signal averaging is no longer feasible to enhance sensitivity and there may be significant fluctuations between successive single-shot multiplex build up and decay transients during the optical cavity sweep cycle.

Figure 12:
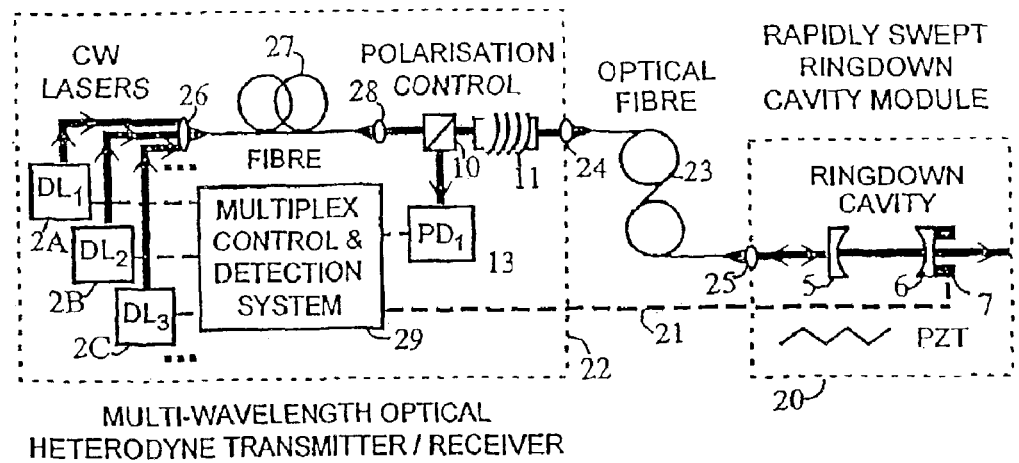
FIG. 12 is a schematic drawing of a single-ended, multiplex, fibre-coupled embodiment of the apparatus combining features of FIGS. 8, 10 and 11.

FIG. 12 depicts a further multiplex embodiment of the invention, in which the optical heterodyne transmitter/receiver section 22 of the apparatus is configured as in FIG. 11 and a single-mode optical fibre 23 is used to couple that section of the apparatus to the rapidly swept ringdown cavity module 20 (as in FIG. 10). These embodiments of the invention as depicted in FIGS. 11 and 12) are intrinsically and uniquely reliant on a rapidly swept ringdown cavity and optical heterodyne detection.

The wavelengths of the various cw lasers ($DL_1$, $DL_2$, ...; 2A, 2B, ...) in FIGS. 11 and 12 need to be separated by optical frequency intervals that exceed the response frequency or bandwidth of the photodetector ($PD_1$) 13, in order to avoid complications from unwanted difference frequencies. For typical photodetectors, this bandwidth limit is typically less than a few GHz. In optical fibre-based implementations of this invention (such as that in FIG. 12), it is feasible to use standard telecommunication optical fibre that is optimised for the shortest wavelength (highest optical frequency) of the set of cw lasers ($DL_1$, $DL_2$, ...) used. The other longer wavelengths (lower optical frequencies) of the remainder of the set is then above the cut-off wavelength of the optical fibre, so that the fibre remains single-mode for radiation from the entire set of cw lasers ($DL_1$, $DL_2$, ...; 2A, 2B, ...) used. For example, an optical fibre designed for single-mode operation in the telecommunications C band at a near infrared wavelength in the range 1.53–1.57 $\mu$m can serve as a single-mode fibre at longer wavelengths with acceptable transmission characteristics extending to longer infrared wavelengths (2.5 $\mu$m and beyond, say).

The wavelength (or optical frequency) dependence of other components in a multi-wavelength optical heterodyne cw-CRDS apparatus as in FIGS. 11 and 12 also needs to be considered. The ringdown cavity mirrors 5, 6 can be made with high-reflectivity dielectric coatings optimised for a particular wavelength but still yielding acceptably high reflectivity over the range of wavelengths (typically 1.5–2.5 $\mu$m) of the set of cw lasers ($DL_1$, $DL_2$, ...; 2A, 2B, ...) used. Such wavelength dependence of mirror reflectivity causes the empty-cell ringdown time to vary for each of the cw lasers ($DL_1$, $DL_2$, ...; 2A, 2B, ...), with longest ringdown times for the wavelength(s) at which the mirror reflectivity is optimised; this variation is readily taken into account in the CRDS analysis procedure. The polarisation control optics section 10, 11 of the multi-wavelength optical heterodyne cw-CRDS apparatus as in FIGS. 11 and 12 typically comprises a polarising beam splitter and either a Faraday rotator or a quarter-wave optical retarder. Prism polarisers are available for use over a wide range of wavelengths, although other types (e.g., thin-film plate polarisers) are efficient over a more limited wavelength range. The rotation angle of a Faraday rotator and the quarter-wave thickness of an optical retarder plate are each dependent on the wavelength (or optical frequency) of the light and therefore are designed with a centre wavelength appropriate for one of the wavelengths (or optical frequencies) of the set of cw lasers ($DL_1$, $DL_2$, ...; 2A, 2B, ...) used and acceptable characteristics at other wavelengths in the set. The polarisation control optics unit 10, 11 therefore has a reduced coupling efficiency for backward-propagating light at wavelengths far removed from the unit's designed centre wavelength, limiting the optical power reaching the photodetector ($PD_1$) 13 and reducing the signal-to-noise ratio accordingly. The transmission characteristics of optical materials (such as fused silica) also limit the range of wavelengths that are applicable, but this is not a severe restriction in the near-infrared and visible regions, where the invention's initial implementations concentrate. For instance, standard silica-core optical fibre typically has an attenuation characteristic of 3 dB per kilometer over the wavelength ranges of 0.90–1.42 $\mu$m and 1.46–1.90 $\mu$m; special silica-core optical fibres with low OH (hydroxyl) optical absorption are available to minimise transmission losses in the 1.42–1.46 $\mu$m region. The wavelength range of 1.9–3.0 $\mu$m is accessible by using infrared fluoride glass fibres. Other developments in optical fibre materials promise further extension of the accessible wavelength range for future applications.

Figure 13:
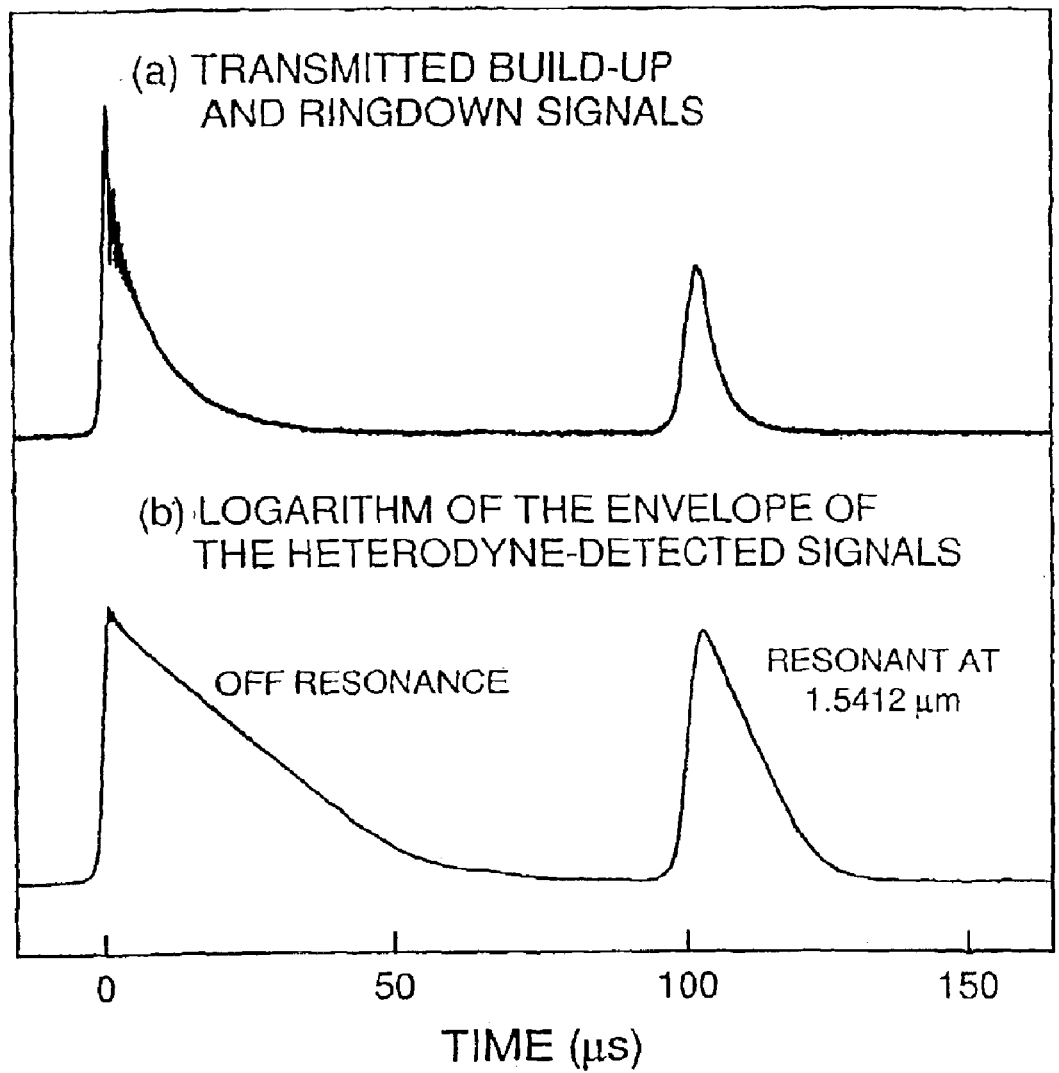
FIG. 13 is a graph of simultaneously recorded multiplex cw-CRDS build-up and ringdown signals with a rapidly swept optical cavity and two separate optical-fibre-coupled tunable diode lasers, one (on the right) preset to resonance with a molecular optical absorption line of interest and the other (on the left) preset off resonance. Each trace is a 256-sweep average respectively recorded (a) by detecting the transmitted signal as in FIGS. 4(a) and (b) by means similar to those for the corresponding optical heterodyne trace (b) of FIG. 9, using an apparatus as in FIG. 12.
Figure 14:
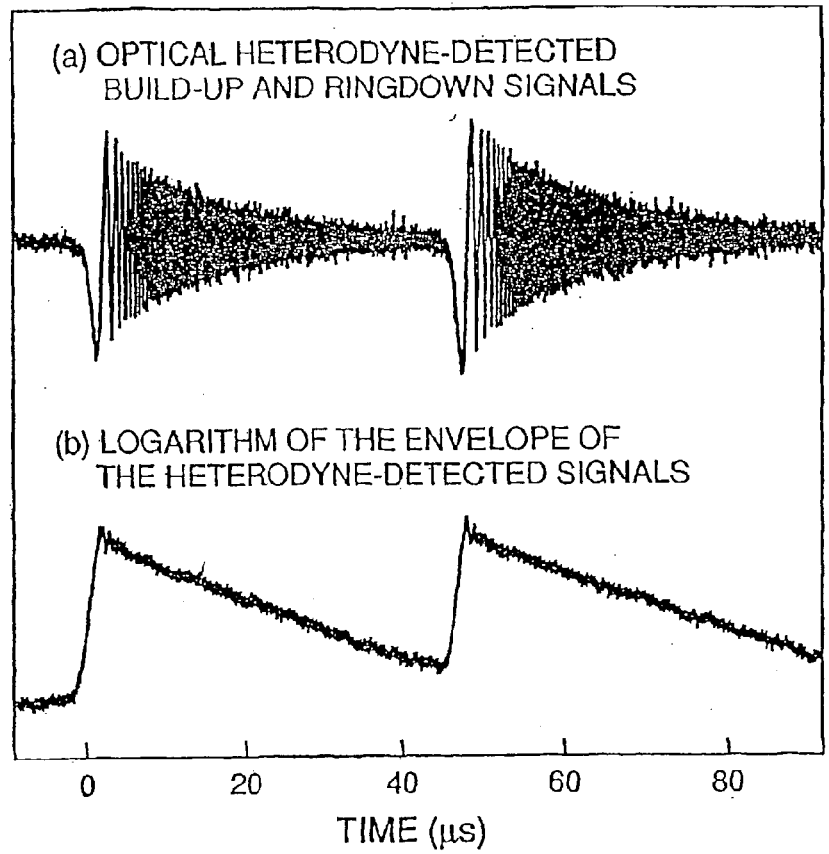
FIG. 14 is a graph of simultaneously recorded multiplex cw-CRDS build-up and ringdown signals with a rapidly swept optical cavity, optical heterodyne detection and two separate optical-fibre-coupled tunable diode lasers, both preset off resonance from any molecular optical absorption line and with approximately equal amplitudes. The two traces (a, b) are recorded in a single sweep of the optical cavity by means similar to those for corresponding traces (a, b) of FIG. 9, using an apparatus as in FIG. 12.

FIG. 13 provides a dual-wavelength demonstration of the above multiplex cw-CRDS approach using a rapidly swept optical cavity and two separate optical-fibre-coupled tunable diode lasers in an apparatus configured as in FIG. 12. Each of the two traces (a, b) depicted is a 256-shot average respectively recorded (a) by detecting the transmitted signal as in FIGS. 4(a) and (b) with the same optical heterodyne detector and demodulating logarithmic amplifier as were used to record corresponding trace (b) of FIG. 9. A 12-meter length of optical fibre is used to couple the optical heterodyne transmitter/receiver section of the apparatus to the rapidly swept ringdown cavity module. One of the two TDL wavelengths (yielding build-up and ringdown signals on the right-hand side of the trace) is set at 1.5412 $\mu$m, to coincide with a relatively strong P-branch peak in the 6503-cm$^{-1}$ $(30^01)_I$–$(00^00)$ rovibrational optical absorption band of $CO_2$ gas a pressure of 2 mbar. The other is set at an off-resonance wavelength to yield build-up and ringdown signals (on the left-hand side of the traces) that are effectively those of the empty ringdown optical cavity. The two cw laser intensities were pre-set to yield cw-CRDS signals of approximately equal amplitude when the optical cavity was empty (i.e., before $CO_2$ gas was admitted), as illustrated in FIG. 14. The effect of optical absorption by $CO_2$ molecules is evident as an increase of both amplitude and ringdown time for the right-hand signals. (This is a crude demonstration, in that the reserve cw-CRDS detection sensitivity spans many orders of magnitude). The leading edge of the left-hand build-up and ringdown transient is used to trigger the digital oscilloscope. This auto-triggered (left-hand) transient is more sharply defined than the subsequent (right-hand) transient, owing to a short-term optical frequency instability of approximately ±1 MHz for each TDL employed and the fact that these results were obtained as a 256-sweep average. A set of results recorded in a single sweep of the ringdown cavity (with the two different TDL wavelengths preset off resonance from any molecular optical absorption line and with amplitudes approximately equal) is presented in FIG. 14. The resulting multiplex optical heterodyne cw-CRDS signals were obtained by means similar to those for corresponding traces (a, b) of FIG. 9, using an apparatus as in FIG. 12 but without any sweep-to-sweep averaging.

Many diode lasers as well as photodetector systems have optical fibre connectors and accordingly it is within the scope of the present invention to package the ringdown cavity module with optical fibre connectors so that different parts of the system are connected only via optical cables. This can result in significant miniaturisation, improved robustness and operational simplification of a CRDS system.

Figure 15:
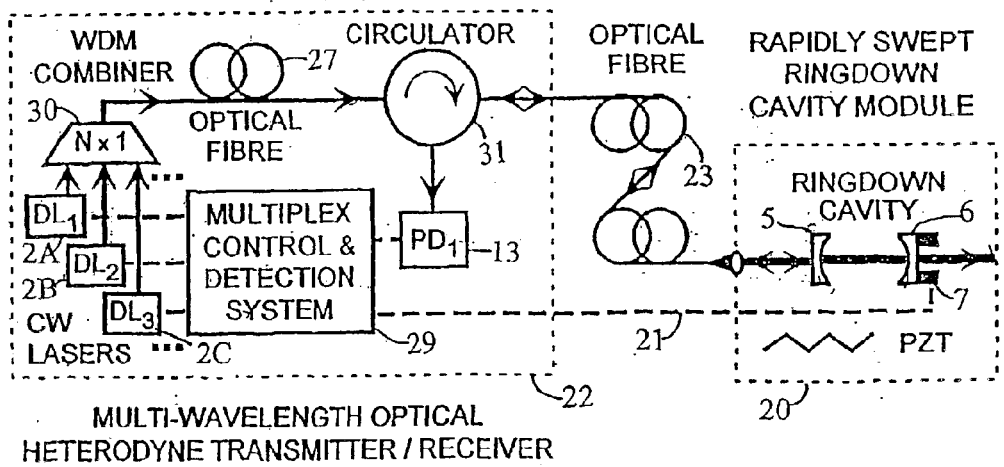
FIG. 15 is a schematic drawing of a single-ended, multiplex, fibre-coupled embodiment of the apparatus similar to FIG. 12, incorporating standard photonics and telecommunications components such as pigtail-coupled diode lasers and optical fibres (replacing discrete microscope objective lenses and fibre-optic micropositioners), a wavelength division multiplexer (to combine the various cw laser beams into one single-mode optical fibre) and an optical circulator.

A further embodiment of the invention is depicted in FIG. 15. As in FIG. 12, the apparatus is single-ended, multiplex, and fibre-coupled, but it is now a more integrated system that incorporates standard photonics components such as pigtail-coupled diode lasers, detectors and optical fibres (replacing discrete microscope objective lenses and fibre-optic micropositioners), optical isolators (integrated into the optical fibres to protect each diode laser from unwanted optical feedback), a wavelength division multiplexer (combining the various cw laser beams into one single-mode optical fibre, by means of a N×1 combiner/multiplexer 30) and an optical circulator 31 (substituting for the function of the polarisation control optics). It is noted that fibre-optic optical circulators are insensitive to variations in the polarisation of the light, which is advantageous in this application. Such photonics devices are widely used for fibre-optical telecommunication instrumentation. The extension shown in FIG. 15 comprises an optical heterodyne cw-CRDS detection system based on an all-fibre-optics based approach. The optical heterodyne transmitter/receiver system and the ring-down cavity module are thereby packaged with optical fibre pigtail connectors so that different parts of the system are linked entirely through optical cables (apart from the ring-down cavity itself, which in intrinsically a free-space optical device requiring a discrete microscope objective lens and fibre-optic micropositioner.

Instead of using optical fibres with multiple wavelengths, one can use in the apparatus of FIGS. 11 and 12, beam splitters, dichroic mirrors, other mirrors, reflectors, prisms such as previously described to combine beams of multiple frequencies together in free space. For fixed frequencies, gratings and prism(s) can also be used. Prisms can also be used as non-dispersive reflectors suitably to guide one or more light beams into a microscopic lens and then into an optical fibre. An optical fibre is desirable in the methods and apparatus of the invention because passing all the multiple laser beams through a single-mode optical fibre has the advantage of using the single-mode fibre as a spatial beam filter. All the beams emerging out of the other end of the single-mode optical fibre share a well-defined beam profile.

EXAMPLE 2

We now consider a second detailed example to illustrate the application of multi-wavelength optical heterodyne cw-CRDS by means of apparatus of the form depicted in FIGS. 11, 12 and 15. The example concerns simultaneous detection of the gas-phase species carbon monoxide (CO) and carbon dioxide ($CO_2$). Measurement of the $CO/CO_2$ ratio in exhaled air can be used to diagnose certain medical conditions. Likewise, the ratio of these two species is a key indicator of combustion processes in industry and the environment, where incomplete combustion or inefficient conversion of hydrocarbon fiels results in higher relative concentration of CO. Spectroscopic, laser-based detection of the $CO/CO_2$ ratio in combustion effluent streams (e.g., industrial smokestacks) offers the prospect of real-time combustion process control and/or environmental monitoring of air quality. For instance, this has already been recognised and implemented in the steel industry, where a tunable mid-infrared diode laser has been used to record spectra in the wavelength region of 4.4–5.3 $\mu$m; here the fundamental (1–0) rovibrational optical absorption band of CO overlaps the $(00^01)_{II}–(00^00)$, $(11^10)_{II}–(00^00)$ and $(11^10)_{II}–(000)$ rovibrational optical absorption bands of $CO_2$ gas. The $CO/CO_2$ ratio is measured by direct transmission of the laser beam through the furnace off-gas and rapidly scanning successive absorption spectra during processes such as oxygen blowing. Results have been reported in the papers: "A laser-based sensor for measurement of off-gas composition and temperature in basic oxygen steelmaking" in *Proc. 81st Steelmaking Conference* (1998) 369–375 and *Scandinavian J. Metallurgy* 28 (1999) 131–137.by D. Otteson, S. Allendorf, P. Ludowise, D. Hardesty, D. Goldstein, T. Miller, C. Smith, M. Bonin; see also U.S. Pat. No. 5,984,998. This approach uses relatively elaborate, fragile lead-salt diode lasers operating in the mid-infrared vicinity of prominent molecular absorption bands.

An alternative approach is to use more readily available, more robust near-infrared diode lasers that access weaker high-overtone or combination bands of gas-phase CO and $CO_2$. The wavelength region of prime interest is the range 1.57–1.59 $\mu$m; here the second overtone (3–0) rovibrational optical absorption band of CO overlaps the $(30^01)_{II}–(00^00)$ rovibrational combination band of $CO_2$ gas, enabling prominent spectroscopic features characteristic of CO and $CO_2$ to appear side by side in relatively short spans of the near-infrared spectrum. This has been realised in trials with multipass absorption cells and laser modulation techniques employed to enhance detection sensitivity. For instance, see the papers: "Observation of CO and $CO_2$ absorption near 1.57 $\mu$m with an external-cavity diode laser" in *Applied Optics* 36 (1997) 3298–3300 by D. M. Sonnenfroh, M. G. Allen; "Diode laser sensor for measurements of CO, $CO_2$, and $H_2O$ in combustion flows" in *Applied Optics* 36 (1997) 8745–8752 by R. M. Mihalcea, D. S. Baer, R. K. Hanson. An analogous study has been made in the vicinity of the second overtone (2–0) absorption band of CO at 2.3–2.4 $\mu$m: "In situ combustion measurements of CO diode-laser absorption near 2.3 $\mu$m" in *Applied Optics* 39 (2000) 5579–5589 by J. Wang, M. Maiorov, D. S. Baer, D. Z. Garbuzov, J. C. Connolly, R. K. Hanson.

The multi-wavelength variant of the optical heterodyne cw-CRDS technique, as in this invention, is expected to offer even higher sensitivity as a way to measure $CO/CO_2$ ratios by means of near-infrared diode lasers. The advantage of a multiplex method such as this is that the concentration of each of the species of interest is measured virtually simultaneously, rather than needing to scan from one characteristic wavelength to another. A non optical heterodyne multiplex cw-CRDS study (in which acousto-optic modulators toggle between two 1.4-$\mu$m diode lasers tuned to absorption lines of vapour-phase species such as methanol and isopropanol) has been reported: "Multiplexed continuous-wave diode-laser cavity ringdown measurements of multiple species" in *Applied Optics* 39 (2000) 2009–2016 by G. Totschnig, D. S. Baer, J. Wang, F. Winter, H. Hofbauer, R. K. Hanson. An implementation of the more advanced multi-wavelength optical heterodyne cw-CRDS approach is outlined below.

In the implementation of multi-wavelength optical heterodyne cw-CRDS to be outlined, two cw tunable diode lasers (TDL) are used, each tuned to characteristic features in the near-infrared absorption spectra of CO and $CO_2$, respectively. In an extension of this approach, a third TDL, tuned to an off-resonance wavelength, can be used (as in FIG. 13) to provide background or baseline information. Both $CO_2$ and CO gases have optical absorption bands within the wavelength range 1.52–1.69 $\mu$m. Therefore, each TDL source can be of the same type with many other optical components optimised for a common spectral region. Apparatus as in FIG. 11, which provides the simplest way to do this, is summarised as follows. Output optical beams of two (or three) TDL sources (e.g., New Focus model 6262/6200) are steered parallel to each other, with very small spatial separation; this is achieved by directing the beams from each laser via small right-angle silica prism reflectors (~5 mm in dimensions). The linear polarisation direction of each TDL optical output beam is vertical and they propagate in a horizontal plane. An optical fibre coupler (Newport model F-91ST) equipped with a microscope objective lens (Newport model M-10×) is used to couple each beam into a short length (~1 m) of single-mode silica-core optical fibre (Newport model F-SMF-28). The alignment of the each optical beam is further optimised individually to achieve equal maximum coupling efficiencies into the optical fibre. The laser beams that emerge from the single-mode optical fibre are collinear and co-propagating, forming a composite multi-wavelength beam of coherent light. A second optical fibre coupler (Newport model F-915T) equipped with a second microscope objective lens (Newport model M-10×) is used to couple the optical fibre output into the ringdown cavity. At least two beam-steering reflectors are used between the fibre output coupler and the ringdown cavity, so that the multi-wavelength laser beam can be aligned to the optical axis of the ringdown cavity. The optical path length between the optical fibre output coupler and the centre of the ringdown cavity is typically ~1.2 m. The optical fibre output coupler is adjusted to focus the multi-wavelength coherent beam at the midpoint of the ringdown cavity. An optical fibre polarisation controller (Newport model F-POL-IL) is used to adjust the polarisation orientation of the emerging beam out of the single-mode optical fibre, so that its linear polarisation axis matches that of the polarisation control unit of FIG. 11; this unit is in the form of a standard optical isolator (Optics for Research model IO-4-IR2-HP). Additional optical isolators are typically combined in series to minimise the influence of backward-propagating light upon the TDL sources, which are susceptible to interference and optical damage. In this implementation, the cavity mirrors (Newport model 10CV00SR.70F) are typically separated by an axial distance of 45.4 cm. A low-voltage PZT element (Piezomechanik model 150/20–15/25 VS 35) is used to drive the cavity mirror, in response to an electrical waveform with a typical peak-to-peak amplitude of ~10 V and a typical frequency of ~1 KHz. Either triangular or sinusoidal waveforms are acceptable fonns of PZT ramp signal; CRDS results of similarly high quality are obtained with either waveform. Near the middle of the ramp cycle, the amplitude of the PZT ramp signal is adjusted to make the ringdown cavity to be successively in optical resonance with each of the TDL wavelengths at sweep-time intervals of ~500 $\mu$s. If the two on-resonance TDL wavelengths are to be resonant with the ringdown cavity at a given sweep-time separation (for example, 45 $\mu$s), then the optical frequency of the two TDL light sources should be separated at a predictable factor time the free spectral range (FSR) of the ringdown cavity. For example, if successive build up and decay transients are to be separated by 45 $\mu$s in a sweep period of 500 $\mu$s, the factor by which the FSR is multiplied is [N+(45/500)], where N is an integer. For a 45.4-cm cavity mirror separation, the FSR is ~330 MHz (0.01100 cm$^{-1}$). If one TDL laser is tuned and set to the 1.5412-$\mu$m (6488.355052-cm$^{-1}$) P(18) rovibrational absorption line of the $(30^01)_I$–$(00^00)$ band of $CO_2$ gas, then a second TDL laser can be suitably tuned and set, for example, to either the 1.5673-$\mu$m (6380.3013-cm$^{-1}$) R(8) line or the 1.5776-$\mu$m (6338.5895-cm$^{-1}$) P(3) line in the (3–0) second overtone band of CO gas.

Potential Applications

The apparatus of the invention is suitable for use in any application where it is desirable to determine whether trace absorbable species are present in a sample having an appropriate wavelength for use with a continuous-wave laser or where it is desirable to determine an optical absorption spectrum of a known compound at very low concentration or with very low optical absorption coefficient. Suitable trace species which could be detected by the method and apparatus of the invention include but are not limited to $CO_2$, CO, $H_2O$ vapour, NO, oxygen, hydrogen fluoride, nitrous oxide, hydrogen cyanide, methane, light alkanes, ethylene, acetylene, ethanol, acetaldehyde, ketones, chloroform and $NH_3$ either alone or simultaneously in combination suitably by use of multiple lasers such as described above. The nature of the trace species that can be detected is limited to those species having wavelengths capable of being generated by the specific components such as lasers, optical fibres, polarisation control optics used.

In many industrial processes the concentration of trace species in flowing gas streams must be measured quickly and accurately. Suitable specific applications include use with aluminium smelters to determine gaseous outputs, for measurement of $CO/CO_2$ ratios to optimise combustion or smelting efficiency, for determining methane gas in mines or near natural gas pipelines, to monitor effluents of various kinds in high-temperature furnaces, for identifying hydrocarbons in engines, and for determining the presence of toxic gases such as HF, HCN, nerve gas and phosgene. Another application comprises monitoring of air quality in closed environments such as the interior of an aircraft or spacecraft. Suitably a dust filter is present to remove any dust from a sample gas prior to introduction into the optical cavity. The apparatus of the present invention has the advantage because of its ability to make instantaneous measurements it can anticipate a hazard or potential contaminant before it becomes a problem and affects the quality of the end product. The apparatus and method also have significant applications to scientific research and measurement technology.

The following Table presents a selective survey of representative molecules that are amenable to sensitive, specific detection by optical heterodyne cw-CRDS. The overtone optical absorption wavelength ranges listed are accessible in various compilations of gas-phase infrared spectroscopic data, notably the HITRAN database: "The HITRAN molecular spectroscopic database and HAWKS (HITRAN Atmospheric Workstation): 1996 edition" in *Journal of Quantitative Spectroscopy and Radiative Transfer* 60 (1998) 665–710 by L. S. Rothman, C. P. Rinsland, A. Goldman, S. T. Massie, D. P. Edwards, J.-M. Flaud, A. Perrin, C. Camy-Peyret, V. Dana, J.-Y. Mandin, J. Schroeder, A. McCann, R. R. Gamache, R. B. Wattson, K. Yoshino, K. V. Chance, K. W. Jucks, L. R. Brown, V. Nemtchinov, P. Varanasi. The survey is confined to the laser wavelength range of 1.25–2.5 $\mu$m, where it is feasible to take advantage of available diode lasers, fibre optics and other telecommunications and photonics components. In cases where the invention is used to facilitate multi-species detection by methods explained above, single-mode optical fibres and related optical components are selected with design characteristics to optimise the transmission and processing of the set of laser wavelengths employed within this wavelength range. Also summarised in the Table is a very wide range of potential industrial, environmental, agricultural and medical diagnostic applications for which the invention in its various embodiments offers practical, cost-effective solutions.

Different polarisers are suitably used for different wavelength ranges. Where optical fibres used cannot simultaneously cover all gases present or suspected to be present, it is within the scope of this invention to combine the apparatus with a second apparatus so as to detect these species.

Figure 16:
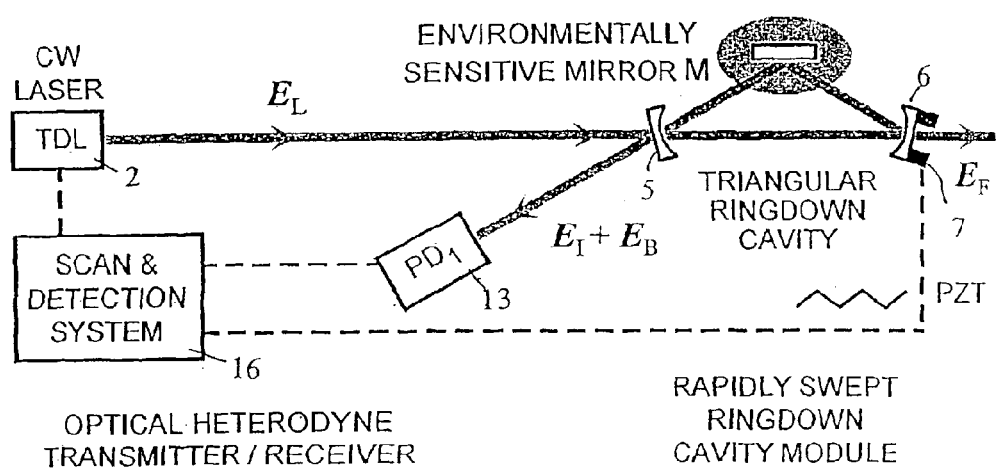
FIG. 16 depicts another embodiment of the apparatus, in which the two-mirror ringdown cavity of FIGS. 1, 5, 8, 10–12 and 15 is replaced by a triangular (or ring) ringdown cavity. The reflectivity of the third mirror (labelled M) is sensitive to its environment (shaded) either inside or outside the cavity or adsorbed on the mirror substrate. Note that the reflected beam, carrying the optical heterodyne cw-CRDS signal, is automatically separated spatially from the incident laser beam by the unidirectional ring cavity, eliminating the need for a polarisation control unit as in FIGS. 1, 5, 8 and 10–12 (or a circulator as in FIG. 15).

The embodiment of the embodiment of the invention depicted in FIG. 16 offers the prospect of measuring samples such as adsorbates or media accessed via evanescent optical waves or environmental factors that affect the reflectivity of a third mirror/reflector in a triangular ringdown cavity. It also eliminates the need for a polarisation control unit or optical circulator, but is less amenable to optical fibre coupling because incident and reflected light beams do not counterpropagate.

Although the present invention has been described hereabove with specific reference to presently preferred configurations and constructions, it will be appreciated that various modification, deletions, additions and alterations may be made to the above-described embodiments without departing from the spirit and scope of the invention.

TABLE

REPRESENTATIVE MOLECULES AMENABLE TO DETECTION BY OPTICAL HETERODYNE cw-CRDS IN THE WAVELENGTH RANGE OF 1.25–2.5 μm

| Gas-Phase Molecule | Overtone absorption wavelength range(s) | Potential areas of application |
|---|---|---|
| Nitric oxide, NO | 1.79–1.82 μm | Neonatal jaundice; asthma; airway constriction marker; blood pressure control; neurophysiology; cardiovascular disease; combustion product |
| Oxygen, $O_2$ | 1.25–1.29 μm | Blood/lung gas-interchange (ratio to $CO_2$); air quality; combustion diagnostics |
| Hydrogen fluoride, HF | 1.25–1.33 μm<br>2.41–2.57 μm | Semiconductor industrial process safety; aluminium smelting exhaust gas |
| Carbon monoxide, CO | 1.56–1.59 μm<br>2.31–2.40 μm | Neonatal jaundice; asthma; blood condition; hæme protein metabolism; nerve transmission; cardiovascular disease; combustion efficiency (ratio to $CO_2$); smokestack pollutant; atmospheric chemistry; ethylene production |
| Carbon dioxide, $CO_2$ | 1.31–1.35 μm<br>1.52–1.55 μm<br>1.57–1.67 μm<br>1.94–2.08 μm | Neonatal jaundice; asthma; gastric, intestinal, pancreatic, liver and bowel disease; blood/lung gas-interchange (ratio to $O_2$); combustion efficiency (ratio to CO); smokestack pollutant; greenhouse gas; overlap with optical absorption bands of minority species in air |
| Nitrous oxide, $N_2O$ | 2.10–2.18 μm<br>2.25–2.29 μm | Anaesthetic gas; combustion fuel; microbial nitrification of soils; greenhouse gas |
| Ammonia, $NH_3$ | 1.50–1.68 μm<br>1.93–2.02 μm<br>2.19–2.35 μm | Agriculture, fertilisers, etc; kidney and liver disease |
| Water vapour, $H_2O$ | 1.26–1.55 μm<br>1.64–2.25 μm | Humidity; natural respiration; combustion; greenhouse gas; overlap with optical absorption bands of minority species in air |
| Hydrogen cyanide, HCN | 1.52–1.55 μm<br>1.84–1.87 μm<br>1.98–2.02 μm | Chemical hazard detection; combustion; atmospheric pollution precursor |
| Methane, $CH_4$ | 1.31–1.35 μm<br>1.62–1.81 μm<br>2.20–2.45 μm | Colon disease; agriculture; dairy cattle health; combustion fuel; greenhouse gas; mine and natural gas supply safety |
| Other light alkanes, $C_nH_{2n+2}$, such as ethane and pentane | 1.4–1.7 μm, etc. | Heart, lung and bowel disease; stroke; arthritis; schizophrenia; multiple sclerosis; vitamin E and trace element deficiency; combustion fuels |
| Ethylene, $C_2H_4$ | 1.7 μm,<br>2.2 μm, etc. | Plant hormone; fruit and vegetable ripening; post-harvest crop storage |
| Acetylene, $C_2H_2$ | 1.49–1.56 μm<br>1.89–1.91 μm | Combustion and welding fuel; ethylene production |
| Ethanol, $C_2H_5OH$ | 1.3–1.4 μm, etc. | Alcohol metabolism; post-harvest crop storage |
| Acetaldehyde, $CH_3CHO$ | 1.80–2.0 μm, etc. | Alcohol metabolism; post-harvest crop storage |
| Ketones, such as acetone, $(CH_3)_2CO$ | 1.7 μm,<br>2.4 μm, etc. | Metabolic stress; cancer indicator; diabetes; blood sugar deficiency; dairy cattle health |
| Chloroform, $CHCl_3$ | 1.5–1.7,<br>2.0–2.3 μm | Anaesthetic gas; solvent exhausts |

What is claimed is:

1. An optical system comprising:
    a ringdown cavity cell, said cell defining a resonant optical cavity;
    means for directing coherent light selected from the group consisting of continuous or quasi-continuous light into said optical cavity,
    means for altering the resonant optical cavity so as to generate a frequency shift of said coherent light in said optical cavity,
    means for coupling said coherent light into said optical cavity,
    means for decoupling the frequency shifted coherent light out of said optical cavity,
    means for optically combining said decoupled frequency shifted coherent light with another portion of coherent light not in optical communication with said optical cavity, and
    means for optical heterodyne detection of the intensity of said combined light.

2. The system according to claim 1 further comprising:
    a coherent light source disposed to enable said means for directing to direct a portion of coherent light from said source into said optical cavity.

3. The system according to claim 2 wherein the coherent light source is a continuous-wave laser.

4. The system according to claim 1 wherein the means of optical heterodyne detection detects intensity as a function of time.

5. The system according to claim 1 wherein the means for altering the resonant optical cavity so as to generate a frequency shift of coherent light in the optical cavity is a piezoelectric translator operated to provide movement of at least one of two reflectors defining the resonant optical cavity, whereby at least one of the reflectors is partially transmitting.

6. The system according to claim 1 wherein the means for directing said portion of coherent light into said optical cavity includes an optical fibre.

7. The system according to claim 1 wherein the means for directing said portion of coherent light into said optical cavity includes an optical circulator.

8. The system according to claim 1 wherein the means for coupling and decoupling is a piezoelectric translator operated to provide movement of at least one of two reflectors defining the resonant optical cavity, whereby at least one of the reflectors is partially transmitting.

9. The system according to claim 1 wherein the means for combining the frequency shifted coherent light with a portion of coherent light not in optical communication with the optical cavity includes an optical fibre.

10. The system according to claim 1 wherein the means for combining the frequency shifted coherent light with a portion of coherent light not in optical communication with the optical cavity includes an optical circulator.

11. The system according to claim 1 wherein the means for optical heterodyne detection is provided by a photodetector.

12. The optical system according to claim 1 further comprising a sample contained in the ringdown cavity cell and means for determining a parameter of the sample.

13. The optical system according to claim 1 wherein more than one coherent light source is used each having a different wavelength and a combiner/multiplexer is provided to combine each wavelength into said ringdown cavity cell.

14. The optical system according to claim 1 which is all-fibre-optic.

15. The optical system according to claim 1 wherein the optical heterodyne detection is a single-ended detection, the frequency shifted light counter-propagating along the same path as the incident coherent light.

16. The optical system according to claim 1 wherein the ringdown cavity cell is in remote optical communication with an optical heterodyne transmitter/receiver.

17. A method for optical detection including emitting coherent light selected from the group consisting of continuous and quasi-continuous light from a coherent light source, directing a portion of said coherent light from said coherent light source to a resonant optical cavity of a ringdown cavity cell, the cell defining a resonant optical cavity in optical communication with the coherent light source, altering the resonant optical cavity so as to generate a frequency shift of coherent light in the optical cavity, coupling said coherent radiation into said optical cavity and decoupling the frequency shifted coherent light out of the optical cavity, optically combining the decoupled frequency shifted coherent light with a portion of coherent light from said coherent light source not in optical communication with said optical cavity and optical heterodyne detecting the intensity of said combined light.

18. A method according to claim 17 further comprising determining a parameter of a sample contained in the ringdown cavity cell.

19. An optical apparatus including:
a continuous-wave laser source for emitting radiation;
a ringdown cavity cell, said cell defining a resonant optical cavity in optical communication with said laser;
means for directing a portion of said radiation emitted from said light source into said optical cavity of said ringdown cavity cell;
means for coupling and decoupling said radiation into said optical cavity without using an optical switch or modulator;
means for generating a frequency shift of the radiation in the optical cavity without using an optical modulator;
means for optically combining a portion of said radiation emitted from said laser source and which has not been emitted from said optical cavity with frequency shifted ringdown cavity radiation which is emitted from the optical cavity, wherein the combined radiation is capable of optical heterodyne detection; and
means for optical heterodyne detection of said combined radiation.

20. A method for optical detection including:
emitting radiation from a continuous-wave laser source;
directing a portion of said radiation emitted from said laser into a resonant optical cavity of a ringdown cavity cell, said resonant optical cavity in optical communication with said laser;
coupling and decoupling said radiation into said optical cavity without using an optical switch or modulator;
generating a frequency shift of the radiation in the optical cavity without using an optical modulator;
optically combining a portion of said radiation emitted from said laser source and which has not been emitted from said optical cavity with frequency shifted ringdown cavity radiation which is emitted from the optical cavity, wherein the combined radiation is capable of optical heterodyne detection; and
optically heterodyne detecting said combined radiation.

21. An optical apparatus including:
at least two continuous-wave laser sources for emitting laser radiation, each source operating at a different wavelength;
a ringdown cavity cell, said cell defining a resonant optical cavity in optical communication with said at least two lasers;
means for directing a portion of said laser radiation emitted from said at least two lasers into said optical cavity of said ringdown cavity cell;
means for coupling and decoupling said laser radiation into said optical cavity;
means for generating a frequency shift of the laser radiation in the optical cavity without using an optical modulator;
means for optically combining a portion of said laser radiation emitted from said laser source and which has not been emitted from said optical cavity with frequency shifted ringdown cavity laser radiation which is emitted from the optical cavity, wherein the combined radiation is capable of optical heterodyne detection; and
means for optical heterodyne detection of said combined radiation.

22. An optical apparatus including:
at least one continuous-wave laser source for emitting laser radiation at a specified wavelength;
at least two ringdown cavity cells, each cell defining a resonant optical cavity in optical communication with at least one of said continuous-wave lasers;
means for directing a portion of said laser radiation emitted from said laser into an optical cavity of at least one of the ringdown cavity cells;
means for coupling and decoupling said laser radiation to said optical cavity;
means for generating a frequency shift of the laser radiation in the optical cavity without using an optical modulator;
means for optically combining a portion of said laser radiation emitted from said laser source and which has not been emitted from said optical cavity with frequency shifted ringdown cavity laser radiation which is emitted from the optical cavity, wherein the combined radiation is capable of optical heterodyne detection; and
means for optical heterodyne detection of said combined radiation.

* * * * *